US009826955B2

(12) United States Patent
Ser et al.

(10) Patent No.: US 9,826,955 B2
(45) Date of Patent: Nov. 28, 2017

(54) AIR CONDUCTION SENSOR AND A SYSTEM AND A METHOD FOR MONITORING A HEALTH CONDITION

(75) Inventors: Wee Ser, Singapore (SG); Jianmin Zhang, Singapore (SG); Jufeng Yu, Singapore (SG); Tongtong Zhang, Singapore (SG)

(73) Assignee: Nanyang Technological University, Singapore (SG)

( * ) Notice: Subject to any disclaimer, the term of this patent is extended or adjusted under 35 U.S.C. 154(b) by 777 days.

(21) Appl. No.: 13/638,163

(22) PCT Filed: Mar. 31, 2011

(86) PCT No.: PCT/SG2011/000136
§ 371 (c)(1),
(2), (4) Date: Dec. 26, 2012

(87) PCT Pub. No.: WO2011/123071
PCT Pub. Date: Oct. 6, 2011

(65) Prior Publication Data
US 2013/0102908 A1    Apr. 25, 2013

(30) Foreign Application Priority Data
Mar. 31, 2010    (SG) ................ 201002250-7

(51) Int. Cl.
*A61B 5/02* (2006.01)
*A61B 7/00* (2006.01)
(Continued)

(52) U.S. Cl.
CPC ............ *A61B 7/003* (2013.01); *A61B 5/0205* (2013.01); *A61B 7/04* (2013.01); *H04R 1/46* (2013.01);
(Continued)

(58) Field of Classification Search
CPC .... H04R 1/406; H04R 1/46; H04R 2201/401; A61B 5/0205; A61B 7/003; A61B 7/04
(Continued)

(56) References Cited

U.S. PATENT DOCUMENTS 4,306,567 A * 12/1981 Krasner .................. 600/484
6,438,238 B1 * 8/2002 Callahan .................. 381/67
(Continued)

FOREIGN PATENT DOCUMENTS

WO    WO2006066337    6/2006

OTHER PUBLICATIONS

Jin et al., "Automatic wheeze detection using histograms of sample entropy," Engineering in Medicine and Biology Society, 2008. EMBS 2008. 30th Annual International Conference of the IEEE, Aug. 2008, pp. 1890-1893.*
(Continued)

*Primary Examiner* — Navin Natnithithadha
*Assistant Examiner* — Eric Messersmith
(74) *Attorney, Agent, or Firm* — K. David Crockett, Esq.; Niky Economy Syrengelas, Esq.; Crockett & Crockett, PC

(57) ABSTRACT

According to embodiments of the present invention, an air conduction sensor for detecting a sound from a user is provided. The air conduction sensor includes a housing comprising an opening, wherein a rim of the opening is configured to at least substantially attach to a skin or a clothing of the user; a microphone coupled to the housing such that there is an air gap between the microphone and the skin or the clothing, and wherein the microphone is configured to detect the sound. A system and a method for monitoring a health condition of a user are also provided.

18 Claims, 30 Drawing Sheets

(51) Int. Cl.
  *A61B 7/04* (2006.01)
  *H04R 1/46* (2006.01)
  *A61B 5/0205* (2006.01)
  *H04R 1/40* (2006.01)

(52) U.S. Cl.
  CPC ........ *H04R 1/406* (2013.01); *H04R 2201/401* (2013.01)

(58) Field of Classification Search
  USPC ........................................ 600/529, 508, 514
  See application file for complete search history.

(56) References Cited

U.S. PATENT DOCUMENTS

| | | | |
|---|---|---|---|
| 6,512,830 B1* | 1/2003 | Orten | .............................. 381/67 |
| 2006/0037615 A1 | 2/2006 | Wilkinson et al. | |
| 2006/0047213 A1 | 3/2006 | Gavriely et al. | |
| 2008/0243017 A1* | 10/2008 | Moussavi | .............. A61B 5/087 600/532 |
| 2010/0256529 A1* | 10/2010 | Grasing et al. | ................ 600/586 |

OTHER PUBLICATIONS

Zhang, et al., A Novel Wheeze Detection Method for Wearable Monitoring Systems, 2009 International Symposium on Intelligent Ubiqutous Computing and Education 331 (May 15, 2009).

Yadollahi, et al., Apnea Detection by Acoustical Means, Proceedings of the 28th IEEE EMBS Annual International Conference, 4623 (Aug. 30, 2006).

Fiz, et al., Detection of Wheezing During Maximal Forced Exhalation in Patients With Obstructed Airways, 122 Chest 186, (Jul. 1, 2002).

Brown, Entropy Isn't What It Used to Be—Applying Thermodynamics to Respiration in Sleep, 123 Chest 9 (Jan. 1, 2003).

Written Opinion dated Oct. 23, 2015 from Singapore patent application No. 2013073150.

* cited by examiner

1316 = 1317a, 1317b and 1317c

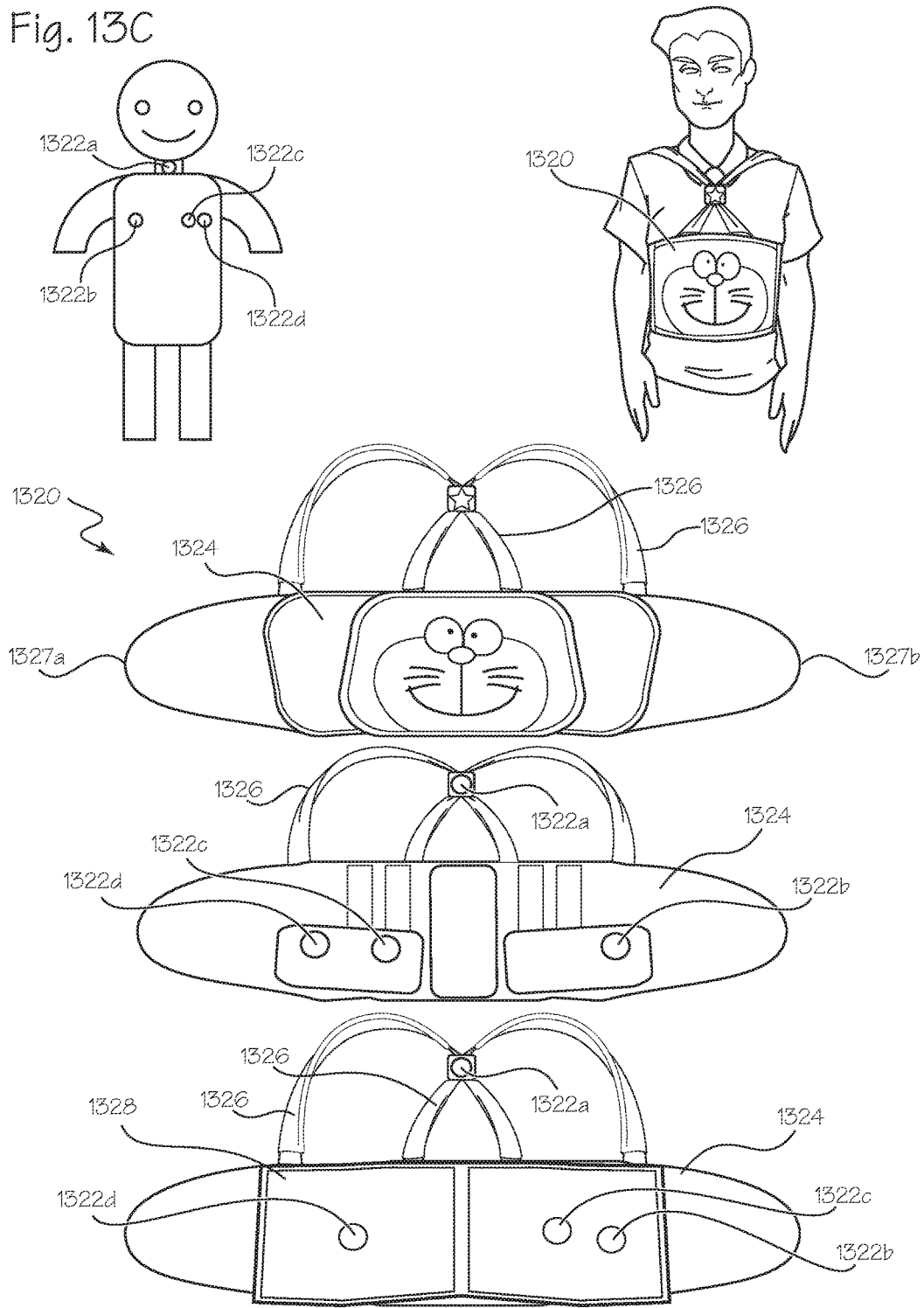

AIR CONDUCTION SENSOR AND A SYSTEM AND A METHOD FOR MONITORING A HEALTH CONDITION

CROSS-REFERENCE TO RELATED APPLICATION

This application claims the benefit of priority of Singapore application No. 201002250-7, filed 31 Mar. 2010, the content of it being hereby incorporated by reference in its entirety for all purposes.

TECHNICAL FIELD

Various embodiments relate to an air conduction sensor for detecting a sound from a user and a method of controlling the air conduction sensor and a system and a method for monitoring a health condition of a user.

BACKGROUND

There is a growing demand for the health condition of patients to be monitored over a long duration. This is true especially for patients with chronic diseases such as asthma. Auscultation using a stethoscope has been the most popular medical tool used for this purpose, but the design of the stethoscope does not allow the monitoring to be made in the absence of a physician. This poses a restriction on the location and duration of the monitoring.

Rapid technological advances in recent years have led to the use of electronic systems for automatic respiration measurement. However, such systems require relatively special equipment and/or bulky equipment that can only be provided in the hospitals. The systems are designed with bundles of wires connecting the equipments to sensors deployed on the human body. These systems attach sensors to the skin of the patients, thereby requiring skin contact of the sensors. All these restrict the movements of the patients, are uncomfortable for the patients and are unsuitable for daily continuous monitoring purposes.

In addition, the computer aided signal detection for wheezes and snores has been investigated for several decades. Many methods have been proposed for this purpose, for example Mel-Frequency Cepstral Coefficients (MFCC), time-frequency analysis, wavelet transform, neural network and Hidden Markov Model (HMM) are among the popular methods. However these methods involve, in general, high computational complexity and are therefore not suitable for implementation for low power and long duration monitoring devices.

SUMMARY

According to an embodiment, an air conduction sensor for detecting a sound from a user is provided. The air conduction sensor may include a housing including an opening, wherein a rim of the opening is configured to at least substantially attach to a skin or a clothing of the user; a microphone coupled to the housing such that there is an air gap between the microphone and the skin or the clothing, and wherein the microphone is configured to detect the sound.

According to an embodiment, a method of controlling an air conduction sensor for detecting a sound from a user is provided. The method may include providing a housing including an opening, wherein a rim of the opening is configured to at least substantially attach to a skin or a clothing of the user; providing a microphone coupled to the housing such that there is an air gap between the microphone and the skin or the clothing, and detecting the sound with the microphone.

According to an embodiment, a wearable portable belt for monitoring a health condition of a user is provided. The wearable portable belt may include a monitoring system including at least one sensor movably arranged in the belt, wherein the at least one sensor is configured to detect at least one sound; and a processing circuit in communication with the at least one sensor, wherein the processing circuit is configured to process the at least one detected sound for monitoring the health condition of the user.

According to an embodiment, a method for monitoring a health condition of a user is provided. The method may include providing a wearable portable belt; providing a monitoring system in the wearable portable belt, the monitoring system including at least one sensor movably arranged in the wearable portable belt and a processing circuit in communication with the at least one sensor; detecting at least one sound with the at least one sensor; and processing the at least one detected sound in the processing circuit for monitoring the health condition of the user.

According to an embodiment, a portable system for monitoring a health condition of a user is provided. The portable system may include a monitoring system including at least two sensors configured to detect at least one sound, wherein the at least two sensors are arranged such that an end-fire direction of the at least two sensors is at least substantially aligned with a central longitudinal axis of the user; and a device in communication with the monitoring system, wherein the device is to configured to process the at least one detected sound for monitoring the health condition of the user.

According to an embodiment, a method for monitoring a health condition of a user is provided. The method may include providing a monitoring system, the monitoring system including at least two sensors; arranging the at least two sensors such that an end-fire direction of the at least two sensors is at least substantially aligned with a central longitudinal axis of the user; detecting at least one sound with the at least two sensors; and processing the at least one detected sound in a device in communication with the monitoring system for monitoring the health condition of the user.

According to an embodiment, a system for monitoring a health condition of a user is provided. The system may include a sensor configured to receive a sound from the user; an analogue-to-digital converter configured to convert the received sound into a digital signal; a selection circuit configured to select samples from the digital signal; an entropy determination circuit configured to determine at least one entropy-based parameter value based on the selected samples; and an entropy comparator circuit configured to compare the at least one entropy-based parameter value with a threshold value to detect a health signal for monitoring the health condition.

According to an embodiment, a method for monitoring a health condition of a user is provided. The method may include receiving a sound from the user; converting the received sound into a digital signal; selecting samples from the digital signal; determining at least one entropy-based parameter value based on the selected samples; and comparing the at least one entropy-based parameter value with a threshold value to detect a health signal for monitoring the health condition.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 13C shows a monitoring system with an array of internal sensors, according to various embodiments.

DETAILED DESCRIPTION

Figure 1:
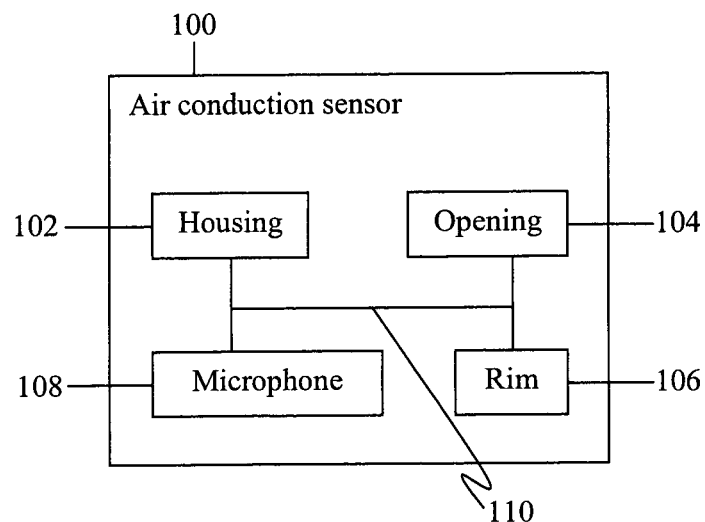
FIG. 1 shows a schematic block diagram of an air conduction sensor for detecting a sound from a user, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

In the context of various embodiments, a 'circuit' may be understood as any kind of a logic implementing entity, which may be special purpose circuitry or a processor executing software stored in a memory, firmware, or any combination thereof. Thus, in an embodiment, a 'circuit' may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A 'circuit' may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

In the context of various embodiments, the term 'main beam direction' as applied to an array of sensors may mean the direction where amplification of a signal is the largest or optimum. In various embodiments, the main beam direction is configured to be at least substantially similar to the direction where the signal of interest is arriving from.

In the context of various embodiments, an 'end-fire direction' as applied to an array of sensors may mean a direction along the axis of the array. In various embodiments, the main beam direction may be at least substantially aligned with the end-fire direction.

In the context of various embodiments, the term 'frequency component' may mean a component in a frequency spectrum or profile. The frequency profile may be a Short Time Fourier Transform (STFT) spectrum. In the context of various embodiments, the term 'power component' may mean a component in a power spectrum.

Various embodiments provide a simple portable monitoring system, and a design or configuration of the system, and a monitoring method, without or with reduced at least some of the associated disadvantages of conventional devices and approaches. The system may be used for the monitoring of health conditions, such as respiratory conditions or disorders for out-patients with conditions such as including, but not limited to, wheezing, stridor, crackles, coughing, asthma, chronic obstructive pulmonary disease (COPD) and obstructive sleep apnea syndrome (OSAS), and cardiac or heart conditions, and diseases relating to heart sounds. The portable system may also be used for various other applications, including evaluating the effectiveness of treatments, training junior physicians and/or medical students, and for medical research purposes.

Various embodiments may provide a portable system including a monitoring system and a device in communication with the monitoring system. The monitoring system includes one or more sensors for detecting sound or sounds from a user. The monitoring system further includes other components such as analogue-to-digital converters and filter to process the detected sounds prior to transmitting the processed sounds to the device for further processing in order to monitor the health condition of the user.

Various embodiments may provide a wearable non-invasive non-skin-contact monitoring system that is configured for automatic detection or monitoring of health conditions (e.g. wheeze) to be performed in the monitoring system or on a portable device (instead of a rack of equipment). The system may be configured to enable the detection or monitoring operation to be performed automatically and continuously over a long duration, and without restricting the user's movements. The monitoring system may be configured to be wearable, to be worn by a patient or user, without the need to connect the system to any external power sources or equipments. Various embodiments may provide the monitoring system in the form of or provided in a flexible wearable belt or vest, designed to allow the user to wear the monitoring system without hindering the user's movements. The wearable design of the system may be flexible and may be used by different sizes of users, for example by using adjustable straps or Velcro to fit different users.

In various embodiments, the monitoring system is a multiple sound-sensor based system designed to detect the presence of respiratory disorder signals generated by the wearer or user. The monitoring system may suppress noises and interferences. In contrast, the presence of noises and interferences in practical environments may affect the operation of a single-sensor system and the results obtained. Therefore, the single-sensor system may not be robust and practical for use in a variety of environments. In various embodiments, a wearable multiple sound-sensor based design for respiration monitoring may be provided.

In the context of various embodiments, the portable system includes a Sensor Sub-System (SES) (e.g. a monitoring system) and a Processing and Recording Sub-System (PRS). The SES may be in electrical communication with the PRS or may communicate wirelessly with the PRS. In various embodiments, the PRS may be integrated in the portable system or may be a portable device (e.g. a personal digital assistant (PDA), a mobile phone or a smart phone). The PRS may include a processor or a processing circuit and storage (e.g. memory).

The SES may include one or more sensors, for example one sensor, two sensors, three sensors, four sensors, five sensors or any higher number of sensors. The sensor or sensors may be housed within a wearable design of the monitoring system. In various embodiments, each of the sensors is connected to, or in electrical communication with a filter and an amplifier. In various embodiments, the SES may further include one or more analogue-to-digital convertors (ADC) in electrical communication with the filter and the amplifier. The ADC may be a single-channel ADC or a multi-channel ADC. The single-channel ADC may be a high speed single-channel ADC in order to sample the output signals of the sensors in turn or consecutively. As the multi-channel ADC provides multiple channels, with each channel configured to sample the output signals of a respective sensor, a multi-channel ADC of any speed may be used.

In various embodiments, the sensor or sensors may be provided in an 'internal configuration' as internal sensor or sensors or in an 'external configuration' as external sensor or sensors. The one or more sensors may be sound sensors or sound-based sensors.

In the context of various embodiments, the term 'internal sensor' may mean an inward-facing sensor directed to the body of the user and is configured to detect or receive sounds originating from within the human body and the term "internal sensors" means a plurality of such sensors.

In various embodiments, internal sensors may be provided at a number of locations or parts of the body (e.g. corresponding to chest, lungs, heart, upper airway, trachea, back) to detect or receive sounds or signals from these parts. The internal sensors may be configured to monitor respiratory signals/disorders or cardiac activities (e.g. through the recording and processing of heart sounds) separately or simultaneously, for example by placing the internal sensors at the chest and/or back areas. Monitoring methods for different respiratory signals and cardiac activities may be developed for various applications.

In various embodiments, the portable system may be a multiple sound-sensor based system configured with internal sensors with temporal filtering (e.g. for noise reduction) to monitor the respiratory conditions at different parts of the body.

In various embodiments, the internal sensors do not require skin contact and therefore the system including the internal sensors may be worn outside the user's clothing.

In the context of various embodiments, the term 'external sensor' may mean an outward-facing sensor directed to the ambient surrounding of the user and is configured to detect or receive sounds or signals from an upper airway, a nose and/or a mouth of the user and sounds from the ambient surrounding (e.g. sounds propagating towards the upper airway) and the term "external sensors" means a plurality of such sensors or an array of such sensors. In various embodiments, the external sensors do not require skin contact and therefore the system including the external sensors may be worn outside the user's clothing.

In various embodiments, the portable system may be a multiple sound-sensor based system configured with external sensors with spatial (e.g. with signal combining using beamforming) and temporal filtering (e.g. for noise reduction) to enhance the quality of the received signals, for respiratory monitoring.

In various embodiments, the external sensors also record or detect noise from the ambient surrounding (e.g. conversations) or unwanted sound generated from the human body, in addition to health-related signals such as the target respiratory sounds from the human body. Therefore, the external sensors may be configured for suppressing these noises or unwanted sounds. As there are a plurality of sensors, these noises or interferences may be suppressed by using suitable adaptive noise cancellation technique, which may not be possible with a single-sensor system.

In addition to monitoring and detecting health-related signals or disorders, such as respiratory signals and/or cardiac signals, the system of various embodiments may be configured for use for other purposes. For example, the portable system with the external sensors may be used to monitor sounds generated in the surroundings and based on these sounds, the system may alert the user of any possible danger surrounding the user. This may be useful for the elderly and/or people with hearing impairments. In addition, the portable system having the external sensors may be configured as a sound recording device for the user.

Furthermore, it should be appreciated that different combinations of the two configurations (i.e. the internal configuration and the external configuration), for example part of or both of these configurations, may be provided. Therefore, any reference to 'a sensor or sensors' includes a reference to a sensor or sensors in the internal configuration, the external configuration or a combination of these configurations.

Further, it should be appreciated that any number of sensors (including one sensor), may be provided. Therefore, any reference to the terms 'internal sensors' and 'external sensors' include a reference to a single sensor in either of these configurations.

In the context of various embodiments, each sensor may convert the sound detected or received by the sensor into an electrical signal.

In the context of various embodiments, each sensor may be a microphone, a stethoscope, a piezo-electric device, a pressure-sensor, or any device that may be used to record sound or sound-generated signals, such that an array or a plurality of sensors may include the same type of sensors or a combination of different types of sensors.

In various embodiments, the microphone may be custom-designed and built. In various embodiments, the stethoscope may be an e-stethoscope or may be custom-designed and built. In various embodiments, where the microphone and stethoscope are custom-designed and built, the microphone and stethoscope may be configured to be used without having contact with the human skin (i.e. the user may wear the system over a thin layer of clothing), thereby allowing the sound signals (e.g. respiratory sound signals) to be recorded or detected even when the user wears a thin layer of clothing underneath the sensors. In various embodiments, the custom-designed microphone may be an air conduction sensor.

In the context of various embodiments, the internal sensors may include the custom-designed microphones, stethoscopes, piezo-electric sensors, pressure sensors, or a combination thereof.

In various embodiments, the operation of the system may involve initially using the sensors in the SES to detect or sense the target sound signals and convert the detected sound signals into electrical signals. The electrical signals are then filtered and amplified and converted into digital signals before being fed to the PRS. The PRS combines the signals, reduces the effects of noises and interferences, extracts the specific parameter values customized according to various embodiments, and uses these parameter values to decide if the target disorder signal (e.g. a respiratory disorder signal) is present or absent. Upon the detection of the presence of the target disorder signal, the extracted parameter values and/or the signals (e.g. sounds) are stored in the PRS. An alert signal may be displayed on the PRS to inform the user or a medical practitioner of the condition. In addition, where a wireless transmission system is provided with the monitoring system, these parameter values and the signals recorded may be transmitted wirelessly to a nearby Internet router for onward transmission to medical practitioners (e.g. doctors), caregivers, clinics, hospitals or databases.

Various embodiments may provide a portable system and a method which enable the use of a single parameter or two parameters for respiration monitoring, for example wheeze detection, instead of a larger number of parameters in conventional systems and/or methods. Various embodiments may provide a system and a method which enable the use of entropy-based parameter(s) for wheeze detection.

Various embodiments may provide a method of detecting the presence of certain types of sound signal. The method may be able to distinguish sound signals with a peculiar energy distribution pattern from those without such a pattern. In various embodiments, the method may detect the existence or presence of sound signals with the peculiar energy distribution pattern in the frequency spectrum or in the power spectrum or in the time-frequency plot using an entropy-based method. In various embodiments, the method requires one single entropy-parameter based feature or two entropy-parameter based features to be calculated, thereby reducing the computational complexity considerably compared to conventional methods (e.g. in time-frequency analysis-based methods, every pixel of the dominant components has to be used in the detection and identification procedure).

In order that the invention may be readily understood and put into practical effect, particular embodiments will now be described by way of examples and not limitations, and with reference to the figures. The embodiments of various modules constituting the portable system and monitoring system of various embodiments are also described. While the descriptions are provided with respect to wheezing and wheeze signals, the system of various embodiments may be configured for detecting or monitoring other respiratory signals, cardiac signals and conditions relating to heart sounds or signals.

FIG. 1 shows a schematic block diagram of an air conduction sensor 100 for detecting a sound from a user, according to various embodiments. The air conduction sensor 100 includes a housing 102 including an opening 104, wherein a rim 106 of the opening 104 is configured to at least substantially attach to a skin or a clothing of the user, a microphone 108 coupled to the housing 102 such that there is an air gap between the microphone 108 and the skin or the clothing, and wherein the microphone 108 is configured to detect the sound. The microphone 108 may be configured to detect the sound from at least one of a lung and a heart of the user. As illustrated by 110, the microphone 108 may be coupled to the housing 102 having the opening 104 and the rim 106 of the opening 104.

In various embodiments, the microphone 108 may be configured to detect the sound in a frequency of between about 20 Hz to about 20 kHz. The microphone 108 may be configured to convert the sound into an electrical signal.

In various embodiments, the air gap may be between about 0.1 cm to about 3 cm.

In various embodiments, the rim 106 of the housing 104 may be configured to cover an area of between about 0.19 cm$^2$ to about 30 cm$^2$. The housing 104 may have a shape of a hemisphere.

In various embodiments, the air conduction sensor 100 may further include a filter and an amplifier in electrical communication with the microphone.

Figure 2:
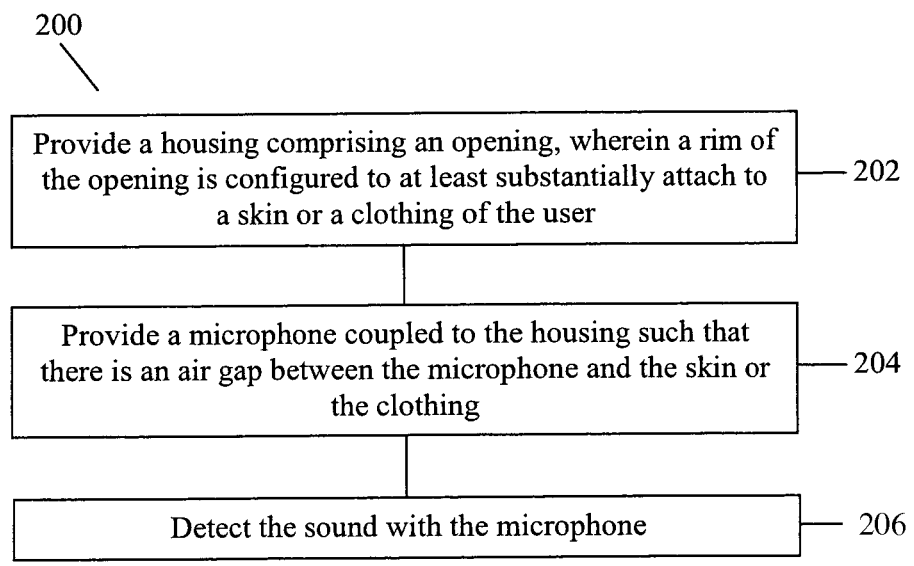
FIG. 2 shows a flow chart illustrating a method of controlling an air conduction sensor for detecting a sound from a user, according to various embodiments.

FIG. 2 shows a flow chart 200 illustrating a method of controlling an air conduction sensor for detecting a sound from a user, according to various embodiments.

At 202, a housing including an opening is provided, wherein a rim of the opening is configured to at least substantially attach to a skin or a clothing of the user.

At 204, a microphone coupled to the housing is provided such that there is an air gap between the microphone and the skin or the clothing.

At 206, the sound is detected with the microphone. The sound may be detected from at least one of a lung and a heart of the user.

In various embodiments, the method may further include converting the sound into an electrical signal.

In various embodiments, the method may further include filtering and amplifying the electrical signal.

In various embodiments, the microphone may be configured to detect the sound in a frequency of between about 20 Hz to about 20 kHz. The air gap may be between about 0.1 cm to about 3 cm.

The rim of the housing may be configured to cover an area of between about 0.19 cm$^2$ to about 30 cm$^2$.

The housing may have a shape of a hemisphere.

Figure 3A:
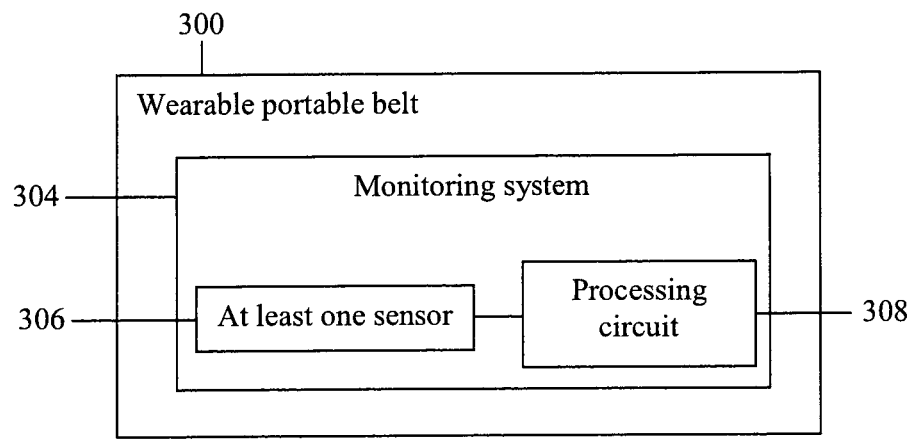
FIG. 3A shows a schematic block diagram of a wearable portable belt for monitoring a health condition of a user, according to various embodiments.

FIG. 3A shows a schematic block diagram of a wearable portable belt 300 for monitoring a health condition of a user, according to various embodiments. The wearable portable belt 300 includes a monitoring system 304. The monitoring system 304 includes at least one sensor 306 movably arranged in the belt 300, wherein the at least one sensor 306 is configured to detect at least one sound, and a processing circuit 308 in communication with the at least one sensor 306, wherein the processing circuit 308 is configured to process the at least one detected sound for monitoring the health condition of the user.

Figure 3B:
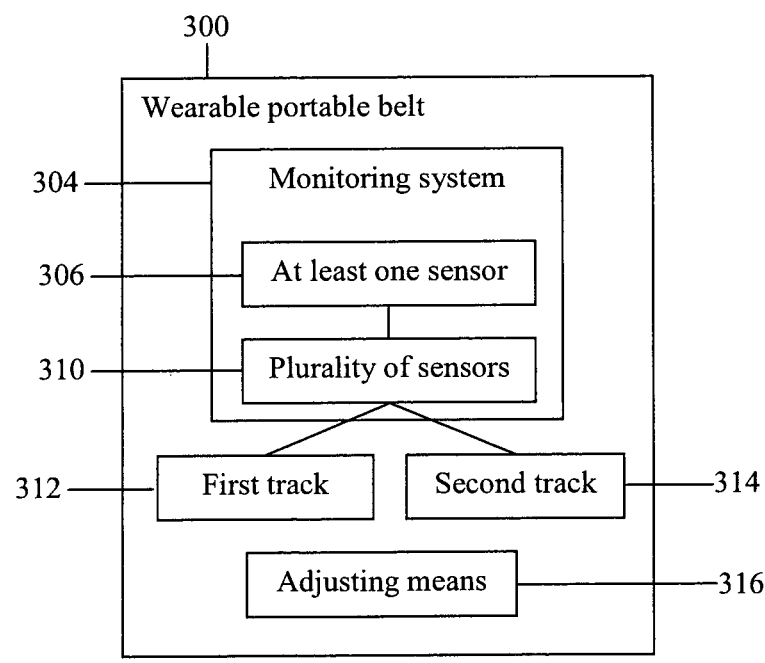
FIG. 3B shows a schematic block diagram of the wearable portable belt of the embodiment of FIG. 3A.

FIG. 3B shows a schematic block diagram of the wearable portable belt 300 of the embodiment of FIG. 3A. In various embodiments, the at least one sensor 306 may be arranged in the belt 300 at a position corresponding to a chest area of the user. The at least one sensor 306 may be configured to detect the at least one sound from at least one of a lung and a heart of the user.

In various embodiments, the at least one sensor 306 may include a plurality of sensors 310. The plurality of sensors 310 may be arranged in the belt 300 at positions corresponding to at least one of a chest area, an upper airway and a back of the user to detect the at least one sound from at least one of the chest area, the upper airway and the back. The plurality of sensors 310 arranged at positions corresponding to the chest area may be arranged at locations corresponding to at least one of a left lung, a right lung and a heart of the user to detect at least one sound from at least one of a left lung, a right lung and a heart. The plurality of sensors 310 arranged at positions corresponding to the chest area may be arranged in a linear array.

The wearable portable belt 300 may further include a first track 312 on a left side of the belt 300 corresponding to a left chest area of the user, and a second track 314 on a right side of the belt 300 corresponding to a right chest area of the user, wherein the plurality of sensors 310 may be movably arranged in at least one of the first track 312 and the second track 314. The wearable portable belt 300 may further include an adjusting means 316 configured to adapt the wearable portable belt 300 to a size of the user. The adjusting means 316 may include at least one of a Velcro fastener and a strap.

Figure 3C:
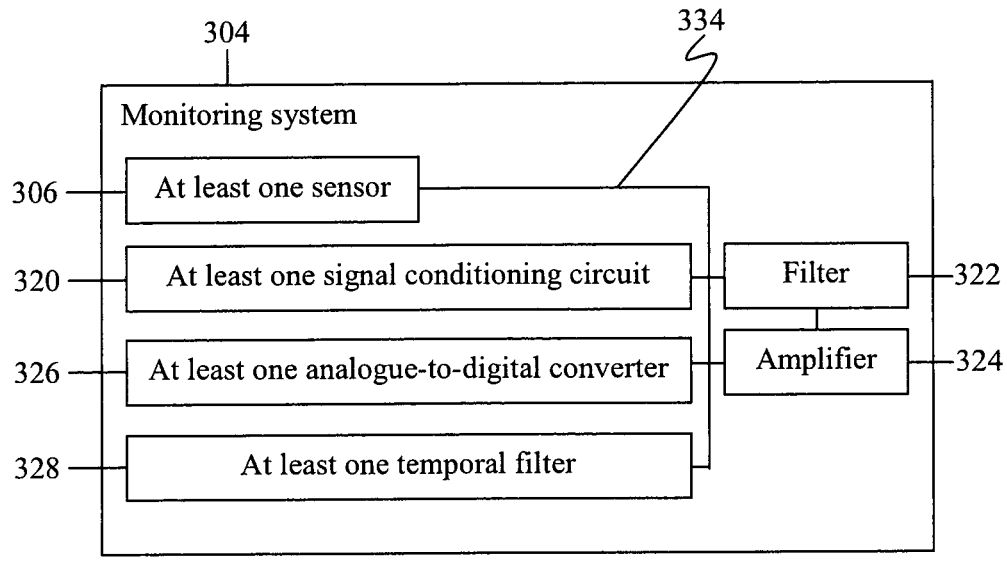
FIG. 3C shows a schematic block diagram of the monitoring system of the embodiment of FIG. 3A.

FIG. 3C shows a schematic block diagram of the monitoring system 304 of the embodiment of FIG. 3A. The monitoring system 304 may further include at least one signal conditioning circuit 320 including a filter 322 and an amplifier 324, wherein a respective signal conditioning circuit of the at least one signal conditioning circuit 320 is in electrical communication with a respective sensor of the at least one sensor 306, and wherein the at least one signal conditioning circuit 320 is configured to filter and amplify a respective detected sound of the at least one detected sound from a respective sensor of the at least one sensor 306 to generate a respective output. In various embodiments, the filter 322 may have a filter bandwidth of one of between about 0 Hz to about 22.063 kHz and between about 60 Hz to about 4000 Hz and a stop-band attenuation of one of between about 10 dB to about 80 dB and about 30 dB. In various embodiments, the amplifier 324 may have a pass-band gain of between 0 dB to about 30 dB.

The monitoring system 304 may further include at least one analogue-to-digital converter 326, wherein a respective analogue-to-digital converter of the at least one analogue-to-digital converter 326 is in electrical communication with a respective signal conditioning circuit of the at least one signal conditioning circuit 320, and wherein the at least one analogue-to-digital converter 326 is configured to convert the respective output into a respective digital signal. In various embodiments, the at least one analogue-to-digital converter 326 may include one of a single-channel analogue-to-digital converter and a multi-channel analogue-to-digital converter. The at least one analogue-to-digital converter 326 may have a sampling rate of one of between about 1000 samples per second (sps) to about 44.125 ksps and about 8000 sps and a resolution of one of between 8 bits to 32 bits and 16 bits.

The monitoring system 304 may further include at least one temporal filter 328, wherein a respective temporal filter of the at least one temporal filter 328 is in electrical communication with a respective analogue-to-digital converter of the at least one analogue-to-digital converter 326, and wherein the at least one temporal filter 328 is configured to filter the respective digital signal to generate a respective filtered output.

In various embodiments, the processing circuit 308 may be configured to receive the respective filtered outputs.

In various embodiments, the at least one sensor 306, the at least one signal conditioning circuit 320, the filter 322, the amplifier 324, the at least one analogue-to-digital converter 326, and the at least one temporal filter 328 may be in communication with each other, as illustrated by 334, for example in electrical communication with each other such as by electrical interconnections (e.g. wire or bus).

Figure 3D:
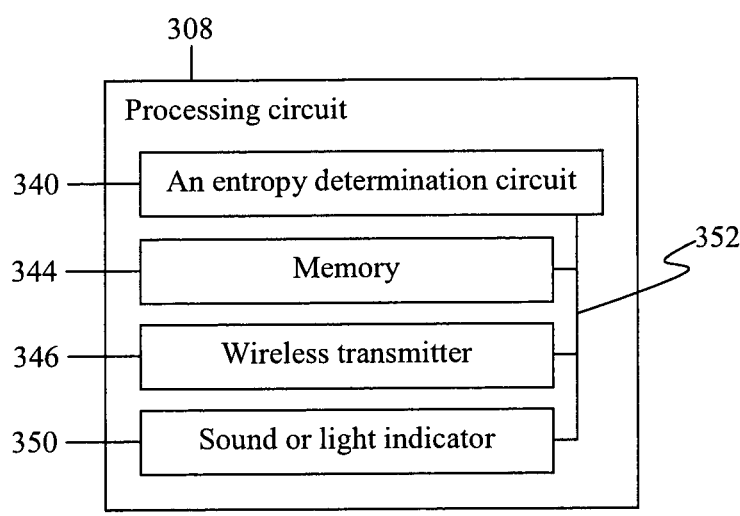
FIG. 3D shows a schematic block diagram of the processing circuit of the embodiment of FIG. 3A.

FIG. 3D shows a schematic block diagram of the processing circuit 308 of the embodiment of FIG. 3A. The processing circuit 308 may include an entropy determination circuit 340 configured to determine at least one entropy-based parameter value from the respective filtered outputs. The at least one entropy-based parameter value may include at least one of an entropy difference between a maximum entropy value and a minimum entropy value and an entropy ratio of a maximum entropy value to a minimum entropy value.

In various embodiments, the processing circuit 308 may further include a memory 344 configured to store at least one of the at least one sound, the respective output, the respective digital signal, the respective filtered outputs and the at least one entropy-based parameter value. The processing circuit 308 may further include a wireless transmitter 346 for communication with an external device. The processing circuit 308 may further include at least one of a sound indicator and a light indicator 350 configured to alert the user of the health condition.

In various embodiments, the entropy determination circuit 340, the memory 344, the wireless transmitter 346, and the at least one of the sound indicator and the light indicator 350, may be in communication with each other, as illustrated by 352, for example in electrical communication with each other such as by electrical interconnections (e.g. wire or bus).

In various embodiments, the at least one sensor 306 may include four sensors. In various embodiments, the at least one sensor 306 may include a sound-based sensor. In various embodiments, the at least one sensor 306 may include at least one of an air conduction sensor, a microphone, a stethoscope, a piezo-electric sensor and a pressure sensor.

In various embodiments, the health condition may include at least one of a respiratory condition and a cardiac condition. In various embodiments, the health condition may include a condition selected from a group consisting of wheezing, asthma, chronic obstructive pulmonary disease, obstructive sleep apnea syndrome, stridor, crackles, coughing and any combination thereof.

In various embodiments, the air conduction sensor 100 of the embodiment of FIG. 1 may be used in the wearable portable belt 300 of the embodiment of FIG. 3A.

Figure 4:
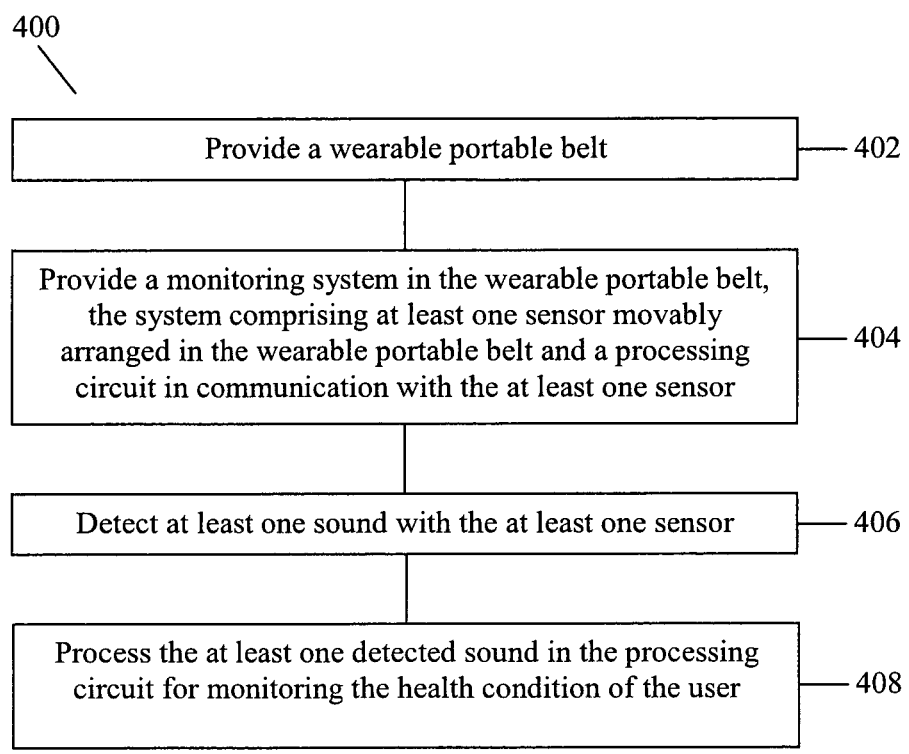
FIG. 4 shows a flow chart illustrating a method for monitoring a health condition of a user, according to various embodiments.

FIG. 4 shows a flow chart illustrating a method 400 for monitoring a health condition of a user, according to various embodiments.

At 402, a wearable portable belt is provided.

At 404, a monitoring system is provided in the wearable portable belt, the system including at least one sensor movably arranged in the wearable portable belt and a processing circuit in communication with the at least one sensor.

At 406, at least one sound is detected with the at least one sensor.

At 408, the at least one detected sound is processed in the processing circuit for monitoring the health condition of the user.

In various embodiments, the at least one sensor may be arranged in the belt at a position corresponding to a chest area of the user.

In various embodiments, the at least one sound may be detected from at least one of a lung and a heart of the user.

In various embodiments, the at least one sensor may include a plurality of sensors. The plurality of sensors may be arranged in the belt at positions corresponding to at least one of a chest area, an upper airway and a back of the user, and the at least one sound may be detected from at least one of the chest area, the upper airway and the back.

In various embodiments, the plurality of sensors arranged in the belt at positions corresponding to the chest area may be arranged at locations corresponding to at least one of a left lung, a right lung and a heart of the user, and the at least one sound may be detected from at least one of a left lung, a right lung and a heart.

In various embodiments, the plurality of sensors arranged at positions corresponding to the chest area may be arranged in a linear array.

In various embodiments, providing the wearable belt may include providing a first track on a left side of the belt corresponding to a left chest area of the user, providing a second track on a right side of the belt corresponding to a right chest area of the user, and movably arranging the plurality of sensors in at least one of the first track and the second track.

In various embodiments, at least one signal conditioning circuit may be provided in the monitoring system, wherein a respective signal conditioning circuit of the at least one signal conditioning circuit is in electrical communication with a respective sensor of the at least one sensor, a filter and an amplifier may be provided in the at least one signal conditioning circuit, and a respective detected sound of the at least one detected sound from a respective sensor of the at least one sensor may be filtered and amplified to generate a respective output. In various embodiments, the filter may have a filter bandwidth of one of between about 0 Hz to about 22.063 kHz and about 60 Hz to about 4000 Hz and a stop-band attenuation of one of between about 10 dB to about 80 dB and about 30 dB. In various embodiments, the amplifier may have a pass-band gain of between 0 dB to about 30 dB.

In various embodiments, at least one analogue-to-digital converter may be provided in the monitoring system, wherein a respective analogue-to-digital converter of the at least one analogue-to-digital converter is in electrical communication with a respective signal conditioning circuit of the at least one signal conditioning circuit, and the respective output may be converted into a respective digital signal. In various embodiments, the at least one analogue-to-digital converter may include one of a single-channel analogue-to-digital converter and a multi-channel analogue-to-digital converter. The at least one analogue-to-digital converter may have a sampling rate of one of between about 1000 sps to about 44.125 ksps and about 8000 sps and a resolution of one of between 8 bits to 32 bits or 16 bits.

In various embodiments, at least one temporal filter may be provided, wherein a respective temporal filter of the at least one temporal filter is in electrical communication with a respective analogue-to-digital converter of the at least one analogue-to-digital converter, and the respective digital signal may be filtered to generate a respective filtered output.

In various embodiments, the respective filtered outputs may be received in the processing circuit.

In various embodiments, at least one entropy-based parameter value may be determined from the respective filtered outputs. In various embodiments, determining the at least one entropy-based parameter value may include determining at least one of an entropy difference between a maximum entropy value and a minimum entropy value and an entropy ratio of a maximum entropy value to a minimum entropy value.

In various embodiments, at least one of the at least one sound, the respective output, the respective digital signal, the respective filtered outputs and the at least one entropy-based parameter value may be stored in a memory in the processing circuit.

In various embodiments, a wireless transmitter may be provided in the processing circuit for communication with an external device.

In various embodiments, the user may be alerted of the health condition by at least one of a sound indicator and a light indicator in the processing circuit.

In various embodiments, the at least one sensor may include four sensors. In various embodiments, the at least one sensor may include a sound-based sensor. In various embodiments, the at least one sensor may include at least one of an air conduction sensor, a microphone, a stethoscope, a piezo-electric sensor and a pressure sensor.

In various embodiments, an adjusting means may be provided in the wearable belt, wherein the adjusting means may be configured to adapt the wearable belt to a size of the user. The adjusting means may include at least one of a Velcro fastener and a strap.

In various embodiments, the health condition may include at least one of a respiratory condition and a cardiac condition. In various embodiments, the health condition may include a condition selected from a group consisting of wheezing, asthma, chronic obstructive pulmonary disease, obstructive sleep apnea syndrome, stridor, crackles, coughing and any combination thereof.

Figure 5A:
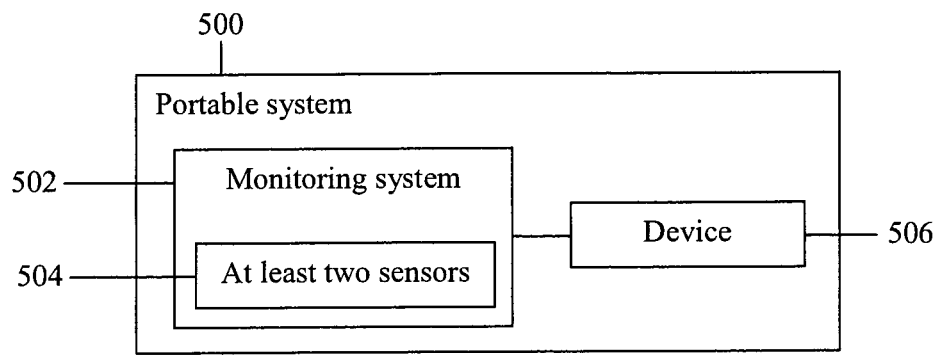
FIG. 5A shows a schematic block diagram of a portable system for monitoring a health condition of a user, according to various embodiments.

FIG. 5A shows a schematic block diagram of a portable system 500 for monitoring a health condition of a user, according to various embodiments. The portable system 500 includes a monitoring system 502 including at least two sensors 504 configured to detect at least one sound, wherein the at least two sensors 504 are arranged such that an end-fire direction of the at least two sensors 504 is at least substantially aligned with a central longitudinal axis of the user, and a device 506 in communication with the monitoring system 502, wherein the device 506 is to configured to process the at least one detected sound for monitoring the health condition of the user.

In various embodiments, the end-fire direction may be at least substantially aligned with a main beam direction of the at least two sensors 504.

In various embodiments, the at least two sensors 504 may be configured to detect the at least one sound from at least one of the user and ambience. In various embodiments, the at least two sensors 504 may be configured to detect at least one sound from at least one of an upper airway, a throat, a mouth, a nose and a chest area of the user.

In various embodiments, the at least two sensors 504 may be arranged in one of a linear array, a grid array and a circular array. The at least two sensors 504 may have an at least substantially uniform spacing between adjacent sensors or a non-uniform spacing between adjacent sensors.

In various embodiments, the portable system 500 may include a housing configured to house the at least two sensors 504.

Figure 5B:
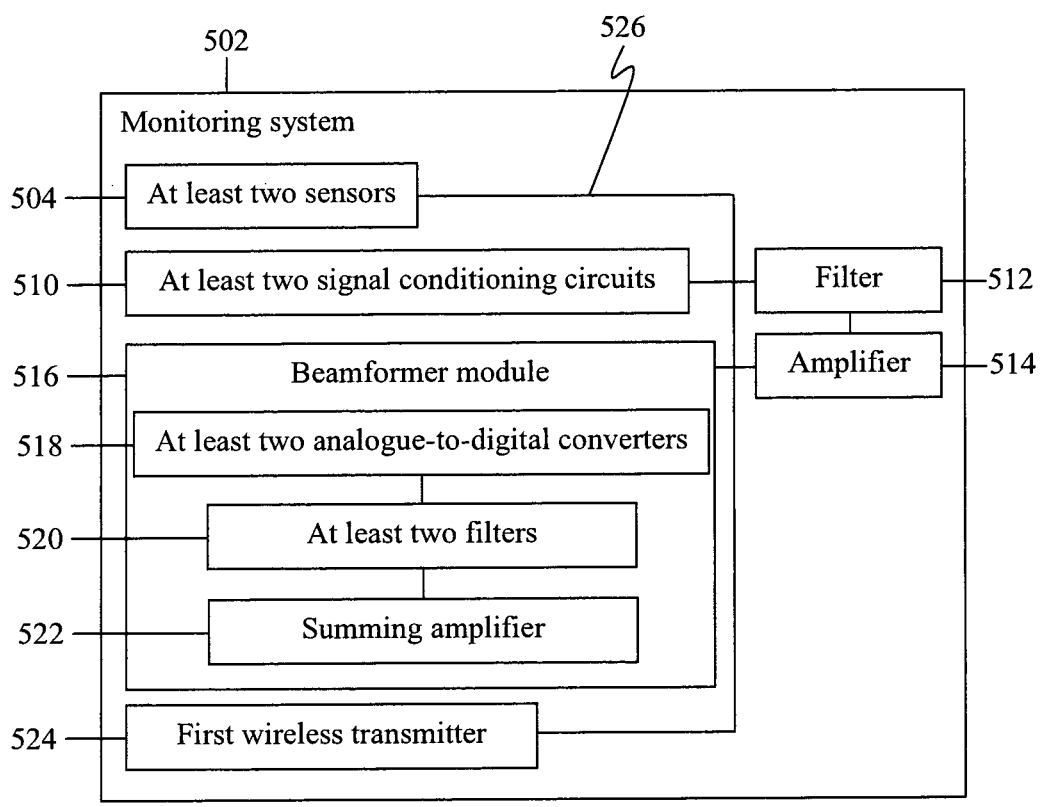
FIG. 5B shows a schematic block diagram of the monitoring system of the embodiment of FIG. 5A.

FIG. 5B shows a schematic block diagram of the monitoring system 502 of the embodiment of FIG. 5A. The monitoring system 502 may further include at least two signal conditioning circuits 510, wherein a respective signal conditioning circuit of the at least two signal conditioning circuits 510 is in electrical communication with a respective sensor of the at least two sensors 504, wherein each of the at least two signal conditioning circuits 510 includes a filter 512 and an amplifier 514, and wherein a respective signal conditioning circuit of the at least two signal conditioning circuits 510 is configured to filter and amplify a respective detected sound of the at least one detected sound from a respective sensor of the at least two sensors 504 to generate a respective output.

In various embodiments, the filter 512 may have a filter bandwidth of one of between about 0 Hz to about 22.063 kHz and about 60 Hz to about 4000 Hz and a stop-band attenuation of one of between about 10 dB to about 80 dB and about 30 dB. In various embodiments, the amplifier 514 may have a pass-band gain of between 0 dB to about 30 dB.

The monitoring system 502 may further include a beamformer module 516 in electrical communication with the at least two signal conditioning circuits 510. The beamformer module 516 may include at least two analogue-to-digital converters 518, wherein a respective analogue-to-digital converter is in electrical communication with a respective signal conditioning circuit of the at least two signal conditioning circuits 510. In various embodiments, each of the at least two analogue-to-digital converters 518 may include one of a single-channel analogue-to-digital converter and a multi-channel analogue-to-digital converter. In various embodiments, each of the at least two analogue-to-digital converters 518 may have a sampling rate of one of between about 1000 sps to about 44.125 ksps and about 8000 sps and a resolution of one of between 8 bits to 32 bits and 16 bits.

The beamformer module 516 may further include at least two filters 520, wherein a respective filter of the at least two filters 520 is in electrical communication with a respective analogue-to-digital converter of the at least two analogue-to-digital converters 518.

The beamformer module 516 may further include a summing amplifier 522 in electrical communication with the at least two filters 520 to generate a sum output. In various embodiments, the device 506 may be configured to receive the sum output.

In various embodiments, the monitoring system 502 may further include a first wireless transmitter 524 for communication with the device 506.

In various embodiments, the at least two sensors 504, the at least two signal conditioning circuits 510, the filter 512, the amplifier 514, the beamformer module 516 and the first wireless transmitter 524 may be in communication with each other, as illustrated by 526, for example in electrical communication with each other such as by electrical interconnections (e.g. wire or bus).

Figure 5C:
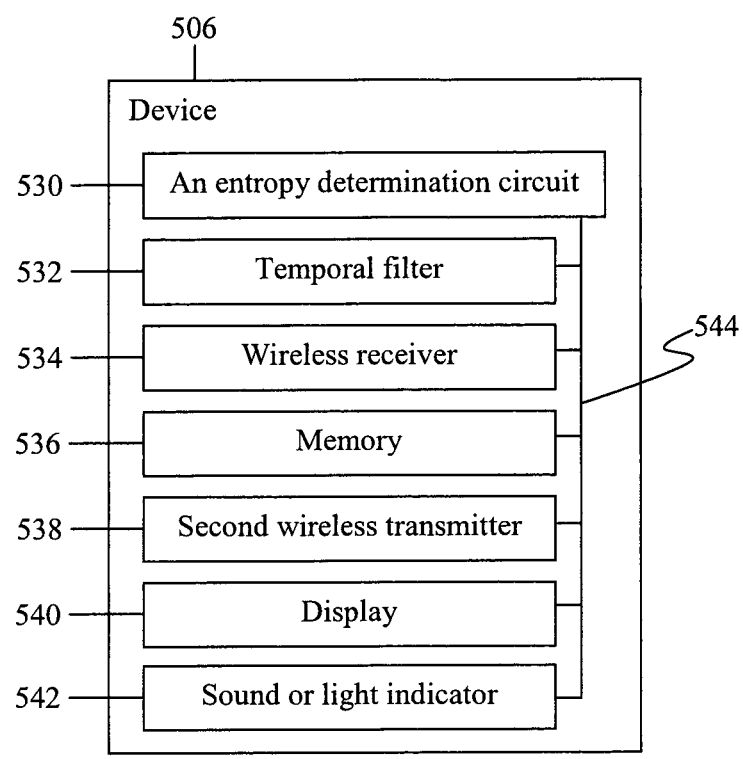
FIG. 5C shows a schematic block diagram of the device of the embodiment of FIG. 5A.

FIG. 5C shows a schematic block diagram of the device 506 of the embodiment of FIG. 5A. The device 506 may include an entropy determination circuit 530 configured to determine at least one entropy-based parameter value from the sum output. The at least one entropy-based parameter value may include at least one of an entropy difference between a maximum entropy value and a minimum entropy value and an entropy ratio of a maximum entropy value to a minimum entropy value.

In various embodiments, the device 506 may further include a temporal filter 532 configured to reduce noise signals from the sum output.

In various embodiments, the device 506 may further include a wireless receiver 532 for communication with the monitoring system 502. The device 506 may further include a memory 536 configured to store at least one of the sum output and the at least one entropy-based parameter value. The device 506 may further include a second wireless transmitter 538 for communication with an external device. The device 506 may further include a display 540 configured to display the health condition. The device 506 may further include at least one of a sound indicator and a light indicator 542 configured to alert the user of the health condition.

In various embodiments, the entropy determination circuit 530, the temporal filter 532, the wireless receiver 534, the memory 536, the second wireless transmitter 538, the display 540 and the at least one of the sound indicator and the light indicator 542, may be in communication with each other, as illustrated by 544, for example in electrical communication with each other such as by electrical interconnections (e.g. wire or bus).

In various embodiments, the device 506 may be a mobile device. In various embodiments, the device 506 may be one of a personal digital assistant (PDA) and a mobile phone.

In various embodiments, the at least two sensors 504 may include four sensors. In various embodiments, each of the at least two sensors 504 may include a sound-based sensor. In various embodiments, the at least two sensors 504 may include at least one of air conduction sensors, microphones, stethoscopes, piezo-electric sensors and pressure sensors.

In various embodiments, the health condition may include at least one of a respiratory condition and a cardiac condition. In various embodiments, the health condition may include a condition selected from a group consisting of wheezing, asthma, chronic obstructive pulmonary disease, obstructive sleep apnea syndrome, stridor, crackles, coughing and any combination thereof.

Figure 6:
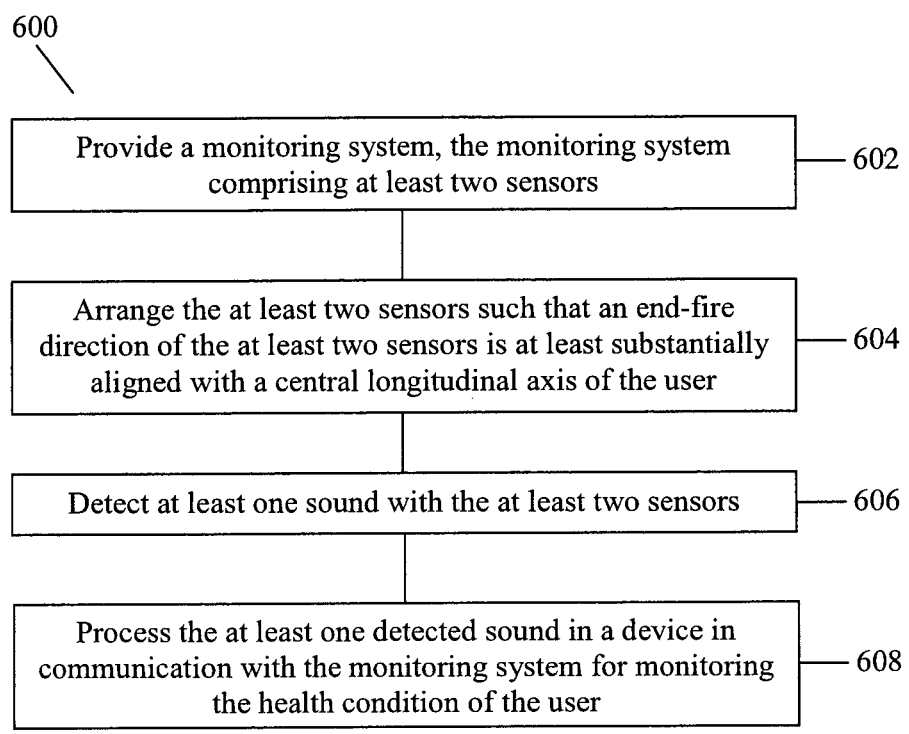
FIG. 6 shows a flow chart illustrating a method for monitoring a health condition of a user, according to various embodiments.

FIG. 6 shows a flow chart 600 illustrating a method for monitoring a health condition of a user, according to various embodiments.

At 602, a monitoring system is provided, the monitoring system including at least two sensors.

At 604, the at least two sensors are arranged such that an end-fire direction of the at least two sensors is at least substantially aligned with a central longitudinal axis of the user.

At 606, at least one sound is detected with the at least two sensors.

At 608, the at least one detected sound is processed in a device in communication with the monitoring system for monitoring the health condition of the user.

In various embodiments, the end-fire direction may be at least substantially aligned with a main beam direction of the at least two sensors.

In various embodiments, the at least one sound may be detected from at least one of the user and ambience. In various embodiments, the at least one sound may be detected from at least one of an upper airway, a throat, a mouth, a nose and a chest area of the user.

In various embodiments, the at least two sensors may be arranged in one of a linear array, a grid array and a circular array. The at least two sensors may have an at least substantially uniform spacing between adjacent sensors or a non-uniform spacing between adjacent sensors.

In various embodiments, a housing may be provided to house the at least two sensors.

In various embodiments, at least two signal conditioning circuits may be provided, wherein a respective signal conditioning circuit of the at least two signal conditioning circuits is in electrical communication with a respective sensor of the at least two sensors, a filter and an amplifier are provided in each of the at least two signal conditioning circuits, and a respective detected sound of the at least one detected sound from a respective sensor of the at least two sensors to generate a respective output is filtered and amplified. In various embodiments, the filter may have a filter bandwidth of one of between about 0 Hz to about 22.063 kHz and between about 60 Hz to about 4000 Hz and a stop-band attenuation of one of between about 10 dB to about 80 dB and about 30 dB. In various embodiments, the amplifier may have a pass-band gain of between 0 dB to about 30 dB.

In various embodiments, a beamformer module may be provided in the monitoring system, wherein beamformer module is in electrical communication with the at least two signal conditioning circuits. In various embodiments, at least two analogue-to-digital converters may be provided in the beamformer module, wherein a respective analogue-to-digital converter is in electrical communication with a respective signal conditioning circuit of the at least two signal conditioning circuits, and the respective output may be converted into a respective digital signal. In various embodiments, each of the at least two analogue-to-digital converters may include one of a single-channel analogue-to-digital converter and a multi-channel analogue-to-digital converter. In various embodiments, each of the at least one analogue-to-digital converter may have a sampling rate of one of between about 1000 sps to about 44.125 ksps and about 8000 sps and a resolution of one of between 8 bits to 32 bits and 16 bits.

In various embodiments, at least two filters may be provided in the beamformer module, wherein a respective filter of the at least two filters is in electrical communication with a respective analogue-to-digital converter of the at least two analogue-to-digital converters, the respective digital signal may be filtered to generate a respective filtered output.

In various embodiments, a summing amplifier may be provided in the beamformer module, wherein the summing amplifier is in electrical communication with the at least two filters to generate a sum output.

In various embodiments, the sum output may be received in the device.

In various embodiments, at least one entropy-based parameter value may be determined from the sum output. In various embodiments, determining the at least one entropy-based parameter value may include determining at least one of an entropy difference between a maximum entropy value and a minimum entropy value and an entropy ratio of a maximum entropy value to a minimum entropy value.

In various embodiments, the sum output may be filtered to reduce noise signals.

In various embodiments, a first wireless transmitter may be provided in the monitoring system for communication with the device.

In various embodiments, at least one of the sum output and the at least one entropy-based parameter value may be stored in a memory in the device.

In various embodiments, a wireless receiver may be provided in the device for communication with the monitoring system. In various embodiments, a second wireless transmitter may be provided in the device.

In various embodiments, the health condition may be displayed in a display in the device. In various embodiments, the user may be alerted of the health condition by at least one of a sound and a light indicator in the device.

In various embodiments, the device may be a mobile device. In various embodiments, the device may be one of a personal digital assistant (PDA) and a mobile phone.

In various embodiments, the at least two sensors may include four sensors. In various embodiments, each of the at least two sensors may include a sound-based sensor.

In various embodiments, the at least two sensors may include at least one of air conduction sensors, microphones, stethoscopes, piezo-electric sensors, and pressure sensors.

In various embodiments, the health condition may include at least one of a respiratory condition and a cardiac condition. In various embodiments, the health condition may include a condition selected from a group consisting of wheezing, asthma, chronic obstructive pulmonary disease, obstructive sleep apnea syndrome, stridor, crackles, coughing and any combination thereof.

Figure 7:
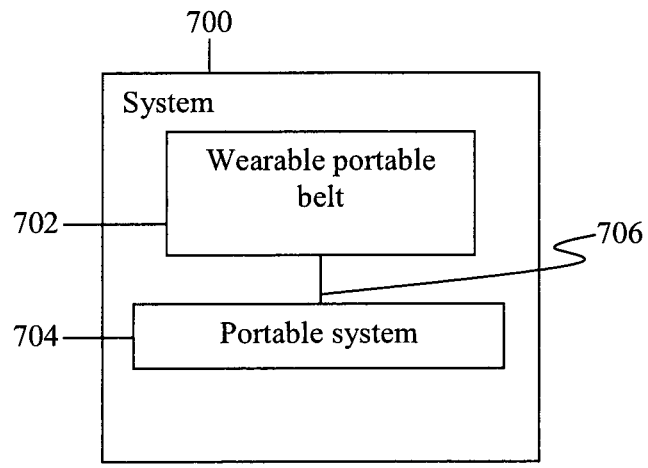
FIG. 7 shows a schematic block diagram of a system for monitoring a health condition of a user, according to various embodiments.

FIG. 7 shows a schematic block diagram of a system 700 for monitoring a health condition of a user, according to various embodiments. The system 700 may include a wearable portable belt 702 and a portable system 704. The wearable portable belt 702 may be of the embodiments of FIGS. 3A to 3D. The portable system 704 may be of the embodiments of FIGS. 5A to 5C. The wearable portable belt 702 and the portable system 704 may be in communication with each other, as illustrated by 706, for example in electrical communication with each other such as by electrical interconnections (e.g. wire or bus).

Figure 8:
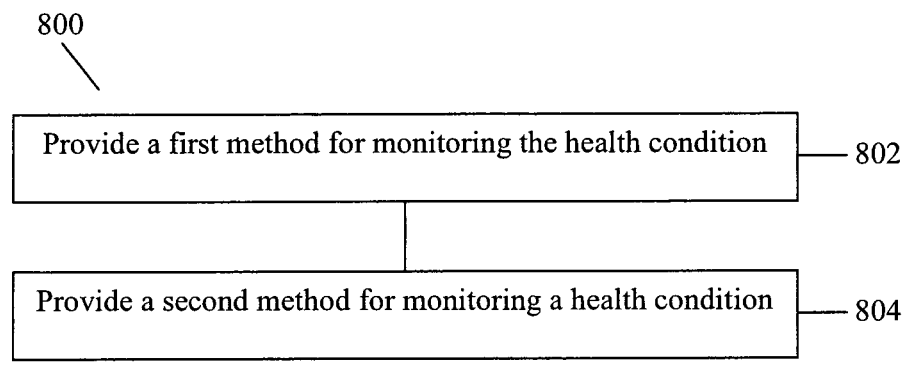
FIG. 8 shows a flow chart illustrating a method of forming a system for monitoring a health condition of a user, according to various embodiments.

FIG. 8 shows a flow chart 800 illustrating a method of forming a system for monitoring a health condition of a user, according to various embodiments.

At 802, a first method for monitoring the health condition is provided.

At 804, a second method for monitoring a health condition is provided.

The first method may be of the embodiment of FIG. 4.

The second method may be of the embodiment of FIG. 6.

Figure 9A:
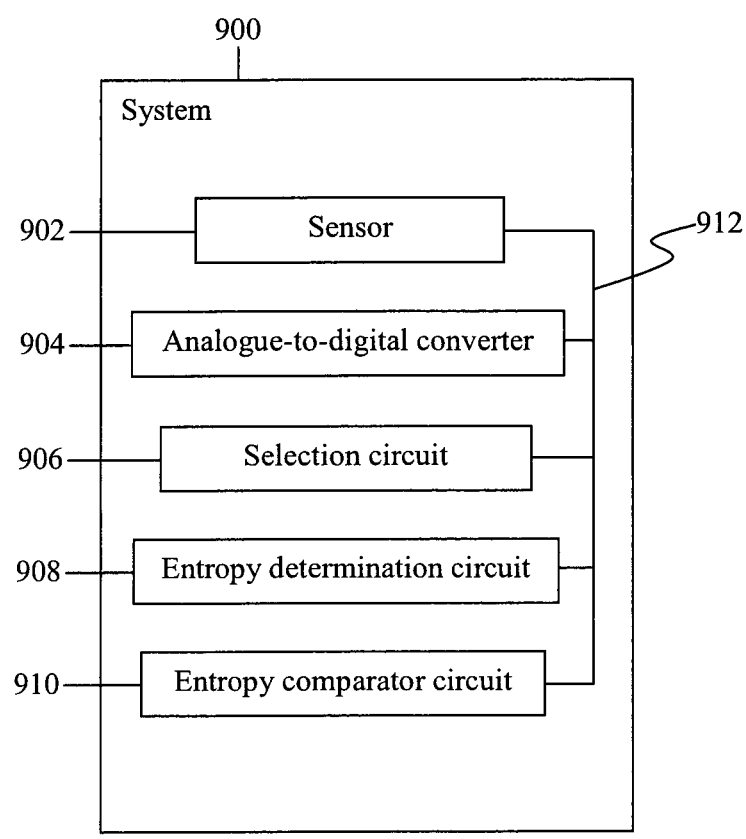
FIG. 9A shows a schematic block diagram of a system for monitoring a health condition of a user, according to various embodiments.

FIG. 9A shows a schematic block diagram of a system 900 for monitoring a health condition of a user, according to various embodiments. The system 900 includes a sensor 902 configured to receive a sound from the user, an analogue-to-digital converter 904 configured to convert the received sound into a digital signal, a selection circuit 906 configured to select a predetermined number of samples from the digital signal, an entropy determination circuit 908 configured to determine at least one entropy-based parameter value based on the selected samples, and an entropy comparator circuit 910 configured to compare the at least one entropy-based parameter value with a predetermined threshold value to detect a health signal for monitoring the health condition.

In various embodiments, the sensor 902, the analogue-to-digital converter 904, the selection circuit 906, the entropy determination circuit 908 and the entropy comparator circuit 910 may be in communication with each other, as illustrated by 912, for example in electrical communication with each other such as by electrical interconnections (e.g. wire or bus).

Figure 9B:
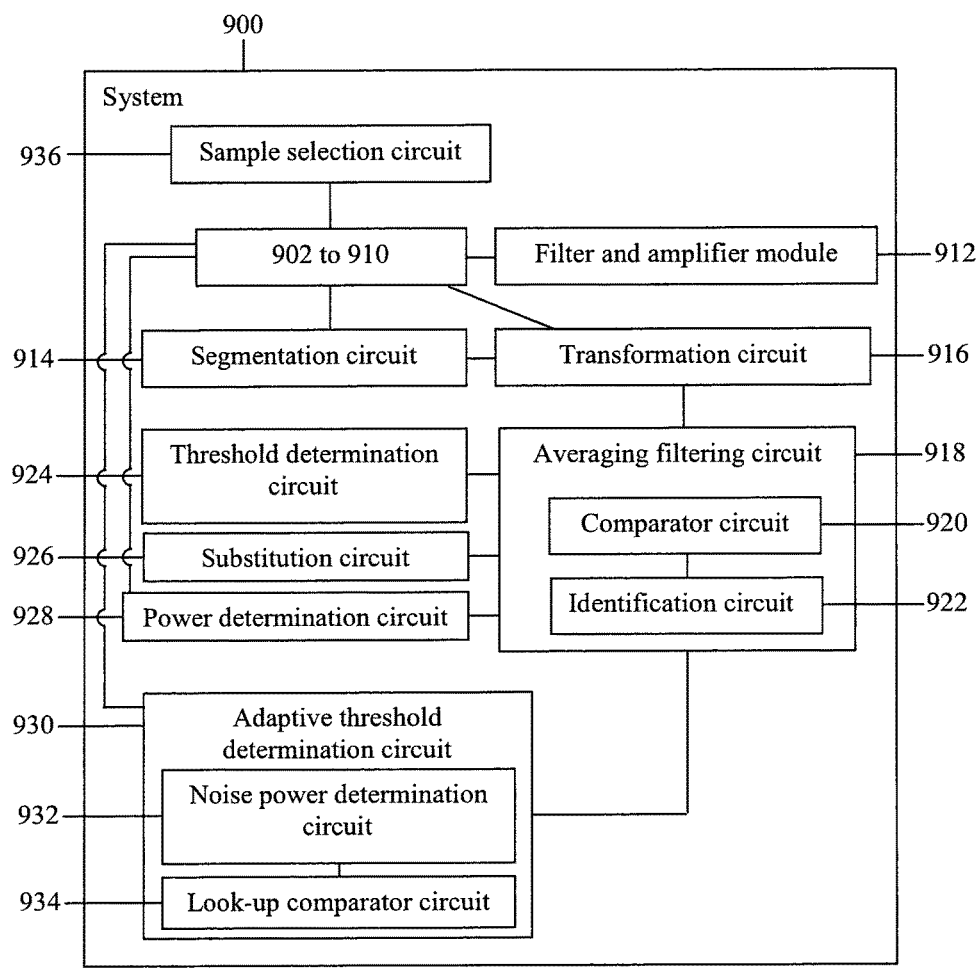
FIG. 9B shows a schematic block diagram of the system of the embodiment of FIG. 9A.

FIG. 9B shows a schematic block diagram of the system 900 of the embodiment of FIG. 9A. In various embodiments, the system 900 may further include a filter and amplifier module 912 configured to amplify the received signal. In various embodiments, the system 900 may further include a segmentation circuit 914 configured to segment the digital signal into a plurality of segments of a first time duration; and wherein the selection circuit 906 is configured to select the samples from the plurality of segments. The first time duration may be one of between about 10 ms to about 1 s and about 64 ms.

In various embodiments, the selected predetermined number of samples may include samples corresponding to one of a segment and an overlap between two adjacent segments of the plurality of segments. The overlap may be one of between about 0% to about 100% and about 50%.

In various embodiments, the system 900 may further include a transformation circuit 916 configured to transform the selected predetermined number of samples into a plurality of frequency components. The transformation circuit may be configured to perform a Short Time Fourier Transform.

In various embodiments, the system 900 may further include an averaging filtering circuit 918 configured to determine a plurality of dominant frequency components.

The averaging filtering circuit 918 may be configured to determine the plurality of dominant frequency components from the plurality of frequency components.

In one embodiment, the averaging filtering circuit 918 may include a comparator circuit 920 configured to compare a respective magnitude of each of the plurality of frequency components with a threshold point, and an identification circuit 922 configured to identify at least one of a dominant frequency component when the respective magnitude is above the threshold point and a non-dominant frequency component when the respective magnitude is below the threshold point. The system 900 may further include a threshold determination circuit 924 configured to determine the threshold point by averaging magnitudes of a predetermined number of neighbouring components of the plurality of frequency components. The predetermined number of neighbouring components may be one of between about 0 to about the predetermined number of samples and about a quarter of the predetermined number of samples.

In another embodiment, the averaging filtering circuit 918 may include a comparator circuit 920 configured to compare a respective magnitude of each of a plurality of power components in a power spectrum corresponding to the plurality of frequency components with a threshold point, and an identification circuit 922 configured to identify at least one of a dominant frequency component when the respective magnitude of the corresponding power component in the power spectrum is above the threshold point and a non-dominant frequency component when the respective magnitude of the corresponding power component in the power spectrum is below the threshold point. The system 900 may further include a threshold determination circuit 924 to determine the threshold point by averaging magnitudes of a predetermined number of neighbouring power components in the power spectrum. The predetermined number of neighbouring power components may be one of between about 0 to about the predetermined number of samples and about a quarter of the predetermined number of samples.

In various embodiments, the non-dominant frequency components may be discarded.

In various embodiments, the system 900 may further include a substitution circuit 926 configured to replace a respective magnitude of each of the non-dominant frequency components with one of about 0.01 and a numeral between about 0 to a value corresponding to a smallest value of the non-dominant frequency components.

In various embodiments, the system 900 may further include a power determination circuit 928 configured to determine a plurality of normalized power of the dominant frequency components.

In various embodiments, the entropy determination circuit 908 may be configured to determine a plurality of entropy values from the plurality of normalized power. The entropy determination circuit 908 may be further configured to determine a maximum entropy value $E_{max}$ and a minimum entropy value $E_{min}$ from the plurality of entropy values after a second time duration. The second time duration may be one of about 3 s and greater than the first time duration. In various embodiments, the at least one entropy-based parameter value may include at least one of an entropy difference $E_d$ between the maximum entropy value $E_{max}$ and the minimum entropy value $E_{min}$ and an entropy ratio $E_r$ of the maximum entropy value $E_{max}$ to the minimum entropy value $E_{min}$.

In various embodiments, the entropy comparator circuit 910 may be further configured to subtract the at least one of the entropy difference and the entropy ratio from the predetermined threshold value to produce a result; and identify that the health signal is present when the result is a positive value or identify that the health signal is absent when the result is a negative value.

In various embodiments, the predetermined threshold value may be one of a fixed threshold value and an adaptive threshold value.

In various embodiments, the system 900 may further include an adaptive threshold determination circuit 930 configured to determine the adaptive threshold value. The adaptive threshold determination circuit 930 may include a noise power determination circuit 932 configured to determine a noise power from the non-dominant frequency components, and a look-up comparator circuit 934 configured to determine the adaptive threshold value based on the noise power and a look-up table including a plurality of predetermined threshold values at different noise powers.

In various embodiments, the system 900 may further include a sample selection circuit 936 configured to reduce the number of samples from the selected predetermined number of samples.

In various embodiments, the analogue-to-digital converter 904 may be configured to sample the received sound at below the Nyquist's sampling rate.

In various embodiments, the sensor 902 may include a sound-based sensor. In various embodiments, the sensor 902 may include one of an air conduction sensor, a microphone, a stethoscope, a piezo-electric sensor and a pressure sensor.

In various embodiments, the health condition may include at least one of a respiratory condition and a cardiac condition. In various embodiments, the health condition may include a condition selected from a group consisting of wheezing, asthma, chronic obstructive pulmonary disease, obstructive sleep apnea syndrome, stridor, crackles, coughing and any combination thereof.

Figure 10:
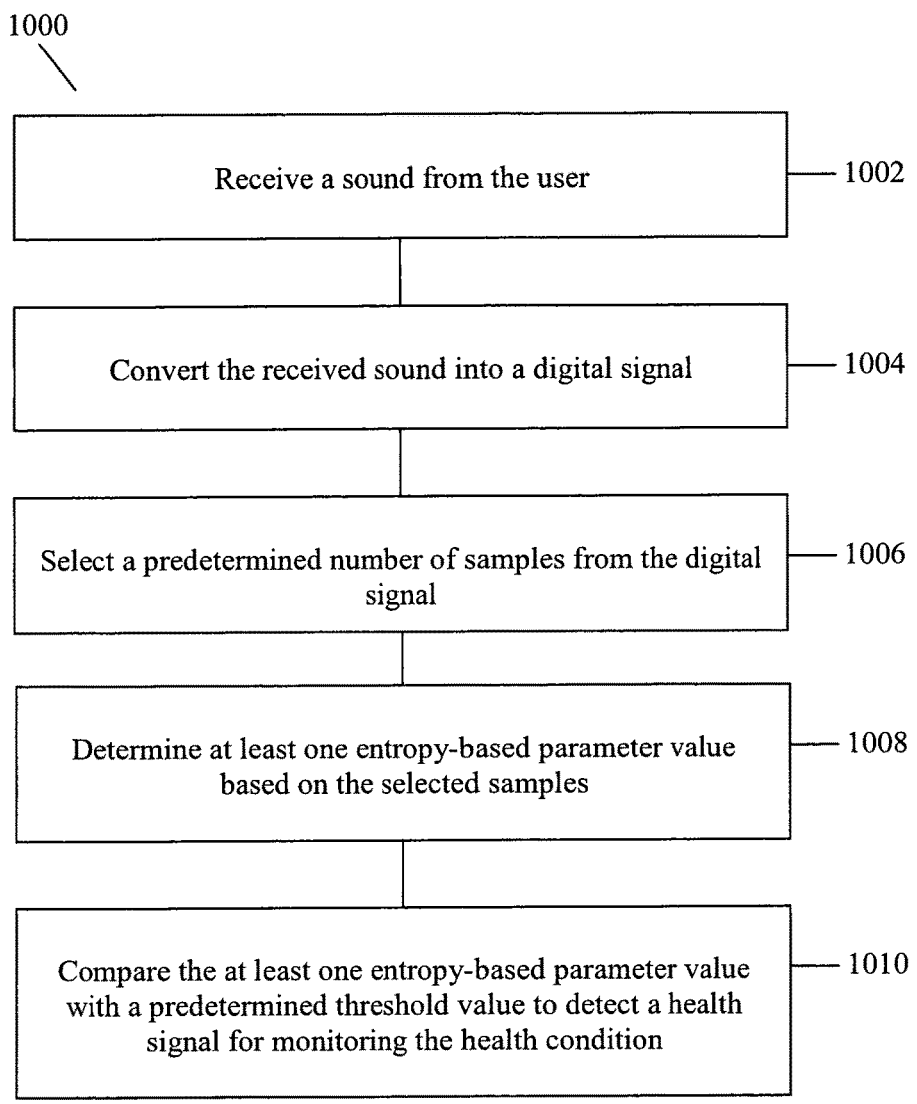
FIG. 10 shows a flow chart illustrating a method for monitoring a health condition of a user, according to various embodiments.

FIG. 10 shows a flow chart 1000 illustrating a method for monitoring a health condition of a user, according to various embodiments.

At 1002, a sound is received from the user.

At 1004, the received sound is converted into a digital signal.

At 1006, a predetermined number of samples are selected from the digital signal.

At 1008, at least one entropy-based parameter value is determined based on the selected samples.

At 1010, the at least one entropy-based parameter value is compared with a predetermined threshold value to detect a health signal for monitoring the health condition In various embodiments, the received sound may be filtered and amplified.

In various embodiments, the digital signal may be segmented into a plurality of segments of a first time duration, wherein the samples may be selected from the plurality of segments. The first time duration may be one of between about 10 ms to about 1 s and about 64 ms.

In various embodiments, the selected predetermined number of samples may include samples corresponding to one of a segment and an overlap between two adjacent segments of the plurality of segments. The overlap may be one of between about 0% to about 100% and about 50%.

In various embodiments, the selected predetermined number of samples may be transformed into a plurality of frequency components. In various embodiments, transforming the selected samples into the plurality of frequency components may include performing a Short Time Fourier Transform.

In various embodiments, a plurality of dominant frequency components may be determined from the plurality of frequency components. In various embodiments, determining the plurality of dominant frequency components includes performing an averaging filtering process.

In one embodiment, performing the averaging filtering process may include comparing a respective magnitude of each of the plurality of frequency components with a threshold point, identifying at least one of a dominant frequency component when the respective magnitude is above the threshold point, and a non-dominant frequency component when the respective magnitude is below the threshold point. The threshold point may be determined by averaging magnitudes of a predetermined number of neighbouring components of the plurality of frequency components. The predetermined number of neighbouring components may be one of between about 0 to about the predetermined number of samples and about a quarter of the predetermined number of samples.

In another embodiment, performing the averaging filtering process may include comparing a respective magnitude of each of a plurality of power components in a power spectrum corresponding to the plurality of frequency components with a threshold point, identifying at least one of a dominant frequency component when the respective magnitude of the corresponding power component in the power spectrum is above the threshold point, and a non-dominant frequency component when the respective magnitude of the corresponding power component in the power spectrum is below the threshold point. The threshold point may be determined by averaging magnitudes of a predetermined number of neighbouring power components in the power spectrum. The predetermined number of neighbouring power components may be between about 0 to about the predetermined number of samples or about a quarter of the predetermined number of samples.

In various embodiments, the non-dominant frequency components may be discarded.

In various embodiments, a respective magnitude of each of the non-dominant frequency components may be replaced with one of about 0.01 and a numeral between about 0 to a value corresponding to a smallest value of the non-dominant frequency components.

In various embodiments, a plurality of normalized power of the dominant frequency components may be determined.

In various embodiments, a plurality of entropy values may be determined from the plurality of normalized power.

In various embodiments, a maximum entropy value $E_{max}$ and a minimum entropy value may be determined from the plurality of entropy values after a second time duration. The second time duration may be one of about 3 s and greater than the first time duration.

In various embodiments, determining the at least one entropy-based parameter value may include determining at least one of an entropy difference $E_d$ between the maximum entropy value $E_{max}$ and the minimum entropy value $E_{min}$ from the equation $$E_d = E_{max} - E_{min}$$

and an entropy ratio $E_r$ of the maximum entropy value $E_{max}$ to the minimum entropy value $E_{min}$ from the equation $$E_r = \frac{E_{max}}{E_{min}}.$$

In various embodiments, comparing the at least one entropy-based parameter value with the predetermined threshold value to detect the health signal related to the health condition may include subtracting at least one of the entropy difference and the entropy ratio from the predetermined threshold value to produce a result, and identifying that the health signal is present when the result is a positive value or identifying that the health signal is absent when the result is a negative value. In various embodiments, the predetermined threshold value may be one of a fixed value and an adaptive value.

In various embodiments, the adaptive threshold value may be determined by determining a noise power from the non-dominant frequency components; and determining the adaptive threshold value based on the noise power and a look-up table including a plurality of predetermined threshold values at different noise powers.

In various embodiments, the number of samples from the selected predetermined number of samples may be reduced.

In various embodiments, converting the received sound into digital signals may include sampling the received sound at below the Nyquist's sampling rate.

In various embodiments, the health condition may include at least one of a respiratory condition and a cardiac condition. In various embodiments, the health condition may include a condition selected from a group consisting of wheezing, asthma, chronic obstructive pulmonary disease, obstructive sleep apnea syndrome, stridor, crackles, coughing and any combination thereof.

Figure 11:
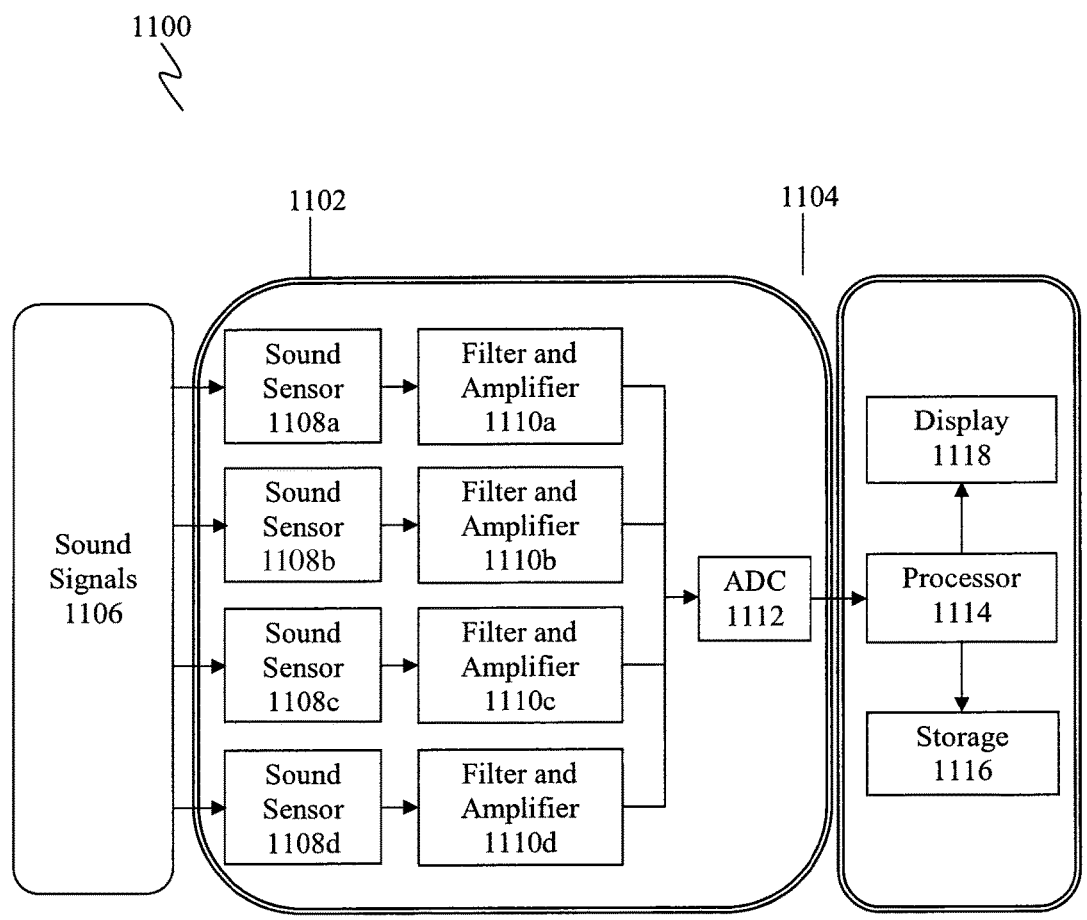
FIG. 11 shows a schematic block diagram of a portable system, according to various embodiments.

FIG. 11 shows a schematic block diagram of a portable system 1100, according to various embodiments. The portable system 1100 includes a Sensor Sub-System (SES) (e.g. a monitoring system) 1102 and a Processing and Recording Sub-System (PRS) 1104. The SES 1102 includes four sound sensors which receive sound signals 1106. The array of four sound sensors include a first sound sensor 1108a, a second sound sensor 1108b, a third sound sensor 1108c and a fourth first sound sensor 1108d, which are each respectively in electrical communication with a first filter and amplifier module 1110a, a second filter and amplifier module 1110b, a third filter and amplifier module 1110c and a fourth filter and amplifier module 1110d.

Each of the first filter and amplifier module 1110a, the second filter and amplifier module 1110b, the third filter and amplifier module 1110c and the fourth filter and amplifier module 1110d is a signal conditioning circuit, including a filter and an amplifier to filter and amplify the sound signals 1106 received.

The SES 1102 may further include an ADC 1112 configured to receive and convert the output signals from the first filter and amplifier module 1110a, the second filter and amplifier module 1110b, the third filter and amplifier module 1110c and the fourth filter and amplifier module 1110d, into digital signals.

The PRS 1104 includes a processor 1114 in communication, either wirelessly or with a cable connection, with the ADC 1112 to perform further processing of the digital signals from the ADC 1112. The PRS 1104 further includes storage (e.g. a memory) 1116 and display 1118 in electrical communication with the processor 1114. The storage 1116 may be used to store data or results while the display 1118 may be used to show the results obtained after processing by the processor 1114.

While FIG. 11 shows that the portable system 1100 includes four sensors (e.g. the first sound sensor 1108a, the second sound sensor 1108b, the third sound sensor 1108c and the fourth first sound sensor 1108d), it should be noted that the portable system 1100 may include any number of sensors, for example, one sensor, two sensors, three sensors, four sensors, five sensors, or any higher number of sensors, with a corresponding number of the filter and amplifier modules.

A sensor configuration according to various embodiments will now be described below, by way of examples and not limitations.

Figure 12A:
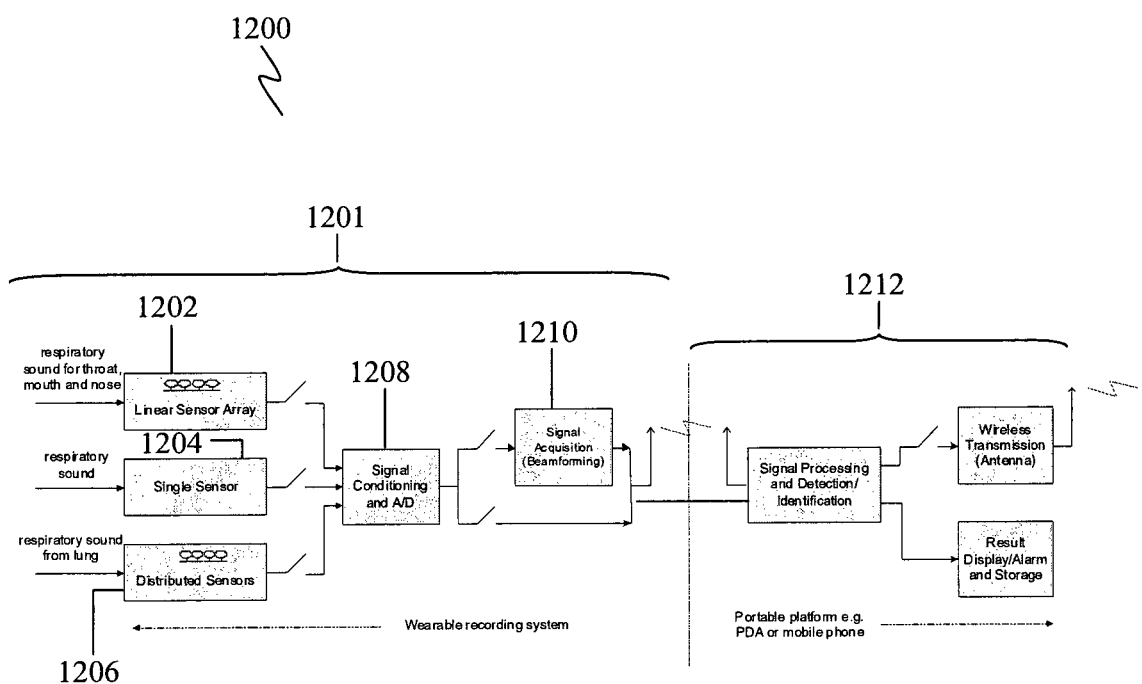
FIG. 12A shows a schematic block diagram of a portable system, according to various embodiments.

Various embodiments may provide a non-invasive sound based wearable health portable system including a monitoring system with one or more external sensors, as shown in FIG. 12A. The sensor may be, for example, a microphone. However, it should be appreciated that other sensor types may be used in the monitoring system, such as a stethoscope, a piezo-electric device, a pressure-sensor, or any device that may be used to record sound or sound-generated signals. In particular, various embodiments may provide a wearable sensor system that is configured to acquire and analyze automatically and continuously the respiratory (and heart beat) sound generated by the user over a long duration and without restraining the user's mobility. The system may be able to detect, identify, and selectively record abnormal sounds (e.g. wheeze) generated by the user, and may transmit the sounds to other devices for further use or processing.

As shown in FIG. 12A, the portable system or node 1200 may include a monitoring system or a recording system 1201. The monitoring system may be wearable and may include a linear sensor array 1202, or a single sensor 1204 or distributed sensors 1206 or any combination thereof. The wearable monitoring system 1201 further includes a signal conditioning circuit and an analogue-to-digital converter, as represented by the block 1208. The wearable monitoring system 1201 may further include a beamformer module, as represented by the block 1210. In various embodiments, the wearable monitoring system 1201 may communicate, for example wirelessly or with a cable connection, with a portable platform or device 1212, such as a PDA or a mobile phone. In various embodiments, by using wireless transmission between the wearable monitoring system 1201 and the portable platform 1212 for the portable system 1200, there is maximum mobility to the user. In addition, the portable platform 1212 may further communicate wirelessly with other devices.

Figure 12B:
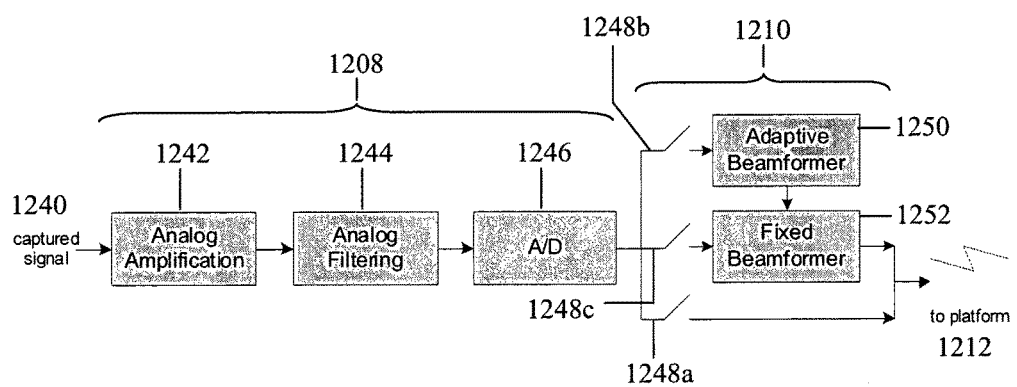
FIG. 12B shows a schematic block diagram of a signal conditioning circuit, an analogue-to-digital converter and a beamformer module of the embodiment of FIG. 12A.

In various embodiments, the signal conditioning circuit and the analogue-to-digital converter, as represented by the block 1208 and the beamformer module 1210 in FIG. 12A may be expanded in further details as shown in FIG. 12B. The signal 1240 captured by the sensor or sensors (e.g. 1202, 1204, 1206 of FIG. 12A) is sent to the signal conditioning circuit 1208 where the signal 1240 undergoes amplification 1242 and filtering 1244 to retain the signal component of interest while removing noise and signal component out of interest. The conditioned signal is then digitized by an analogue-to-digital converter 1246. In various embodiments, the signal 1240 may include a plurality of signals from the array of sensors.

In various embodiments, for example when the single sensor 1204 (FIG. 12A) or the distributed sensors 1206 (FIG. 12A) are used to capture the signal 1240, the digitised signal may be transmitted, for example wirelessly or with a cable connection, to the portable platform 1212 via path 1248a.

In various embodiments, when the linear sensor array 1202 (FIG. 12A) is used to capture the signal 1240, the digitised signal may be enhanced via the beamformer module 1210 configured to remove spatially distributed noise and interferences. The digitised signal may be enhanced by either an adaptive beamformer 1250 via path 1248b or a fixed beamformer 1252 via path 1248c, depending on the application scenario and/or the computational power of the portable system or node 1200 (FIG. 12). An adaptive beamformer may be configured to adjust the main beam direction using the signal 1240 acquired continuously. A fixed beamformer maintains a single main beam direction and does not adjust the main beam direction. At the beamformer module 1210, multiple sensor outputs are combined into a single output to reduce the data rate to be transmitted to the platform 1212, which therefore saves power. The processed signal is then transmitted, for example wirelessly or with a cable connection, to the portable platform 1212.

Figure 13A:
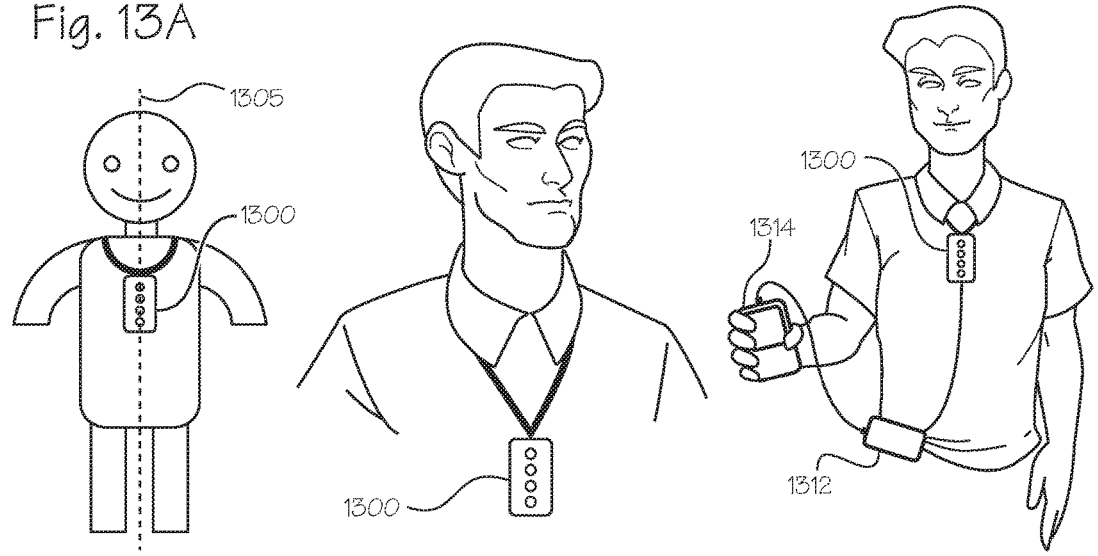
FIG. 13A shows a monitoring system with an array of external sensors, according to various embodiments.
Figure 13A:
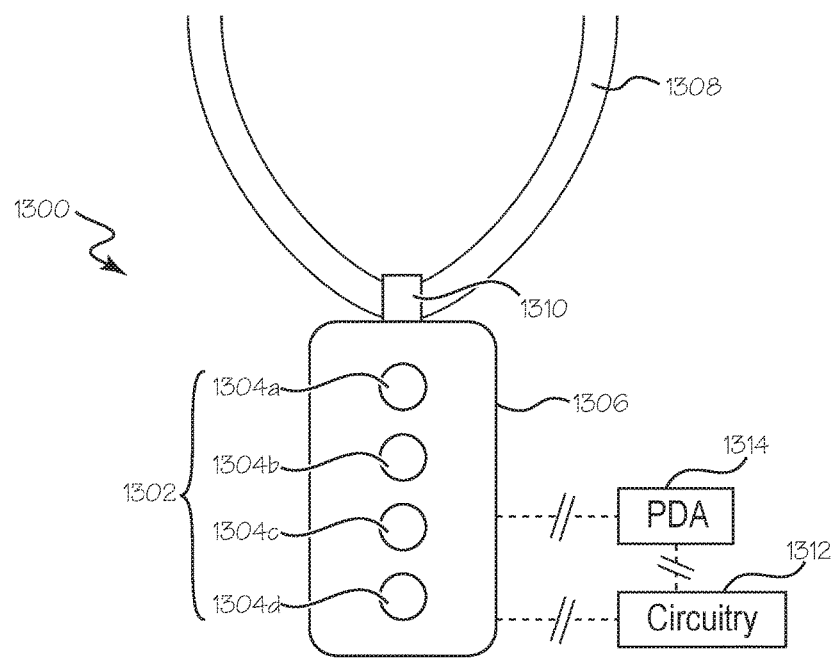
Figure 13B:
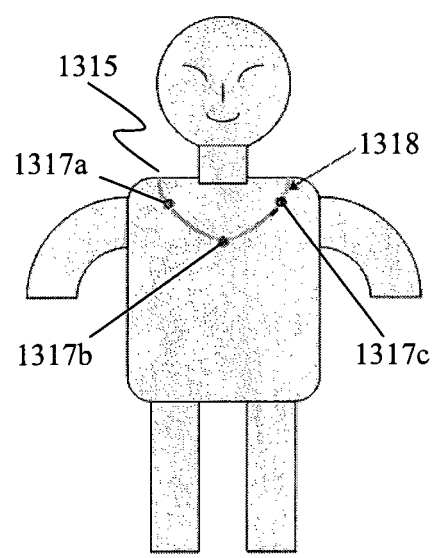
FIG. 13B shows a monitoring system with an array of external sensors, according to various embodiments.

FIGS. 13A and 13B show a respective wearable monitoring system with an array of external sensors, according to various embodiments, configured to capture or detect respiratory sounds, including abnormal respiratory sounds, of the user.

FIG. 13A shows a monitoring system 1300 with an array of external sensors 1302, according to various embodiments. The array of external sensors 1302 may be an SES. The array of external sensors 1302 includes a first sensor 1304a, a second sensor 1304b, a third sensor 1304c and a fourth sensor 1304d. The array of external sensors 1302 is arranged such that an end-fire direction of the array of external sensors 1302 is at least substantially aligned with a central longitudinal axis 1305 of the user. In various embodiments, the main beam direction may be at least substantially aligned with the central longitudinal axis 1305 of the user, and therefore also at least substantially aligned with the end-fire direction of the array of external sensors 1302. In various embodiments, the array of external sensors 1302 is arranged as a linear array with an end-fire configuration for use for beamforming. The linear array of external sensors 1302 may be equivalent to the linear sensor array 1202 (FIG. 12A).

The array of external sensors 1302 is provided in a housing 1306 (e.g. a box), which may be designed as a pendant, including a strap 1308 coupled via a connector 1310 to the housing 1306. The pendant may be worn by a user on the exterior (i.e. outside the user's clothing). In various embodiments, the array of external sensors 1302 may receive or detect respiratory sounds from either the upper airway or the throat, the mouth or the nose or any combination thereof.

The monitoring system 1300 may include a circuitry 1312 in electrical communication with the array of sensors 1302. The monitoring system 1300 may communicate with a PDA 1314 functioning as a Processing and Recording Sub-System (PRS). The monitoring system 1300, including the circuitry 1312 and the PDA 1314 form part of a portable system for monitoring a health condition of the user. The circuitry 1312 may include a signal conditioning circuitry configured to process or manipulate the analogue signals from the first sensor 1304a, the second sensor 1304b, the third sensor 1304c and the fourth sensor 1304d, for subsequent further processing. In various embodiments, the circuitry 1312 may be analogous to the first filter and amplifier module 1110a, the second filter and amplifier module 1110b, the third filter and amplifier module 1110c and the fourth filter and amplifier module 1110d of FIG. 11. The circuitry 1312 may further include an analogue-to-digital converter (ADC) in communication with the signal conditioning circuitry.

For measurement operation, the first sensor 1304a, the second sensor 1304b, the third sensor 1304c and the fourth sensor 1304d are used together as an array of sensors to receive and amplify sounds or sound signals arriving from the end-fire direction, while suppressing noises and interferences from all other directions. In various embodiments, the end-fire direction is designed to be in the direction of the mouth or the upper airway of the user, at least substantially aligned with the central longitudinal axis 1305 of the user.

While FIG. 13A shows a linear array of uniformly-spaced sensors 1302, it should be appreciated that other geometries or configurations, including but not limited to, a circular array of sensors and/or an array of sensors with non-uniform inter-sensor spacings, may be provided or designed. In addition, while FIG. 13A shows an array of 4 sensors 1302, any number of sensors may be provided, depending on the size and shape of the system and wearable design and the application of the system, for example 2 sensors, 3 sensors, 5 sensors, 6 sensors or any higher number of sensors.

FIG. 13B shows a wearable monitoring system 1315 with an array of external sensors 1316, according to various embodiments. The array of sensors 1316 includes a set of distributed sensors including a first sensor 1317a, a second sensor 1317b and a third sensor 1317c, arranged on a pendant 1318, to capture or detect sounds generated from the chest area of the user. The first sensor 1317a and the third sensor 1317c may be positioned respectively, on the right side and the left side of the chest area just below the neck, while the second sensor 1317b may be positioned in the middle of the chest area of the user. The array of sensors 1316 may be equivalent to the distributed sensors 1206 (FIG. 12A).

It should be appreciated that while FIG. 13B shows an array of sensors 1316 having 3 sensors, any number of sensors may be provided, depending on the size and shape of the system and wearable design and the application of the system, for example 2 sensors, 4 sensors, 5 sensors, 6 sensors or any higher number of sensors.

In various embodiments, any combinations of the wearable monitoring system 1300 (FIG. 13A), the wearable monitoring system 1315 (FIG. 13B) and a wearable monitoring system with a single microphone (e.g. equivalent to the single microphone 1204 of FIG. 12A) may be provided.

FIG. 13C shows a wearable monitoring system 1320 with an array of internal sensors 1321, according to various embodiments. The array of internal sensors 1321, include a first sensor 1322a, a second sensor 1322b, a third sensor 1322c and a fourth sensor 1322d. The first sensor 1322a, the second sensor 1322b, a third sensor 1322c and a fourth sensor 1322d, and the corresponding electronic circuits, are arranged and housed within a custom-designed belt or vest 1324. The belt 1324 includes a number of straps 1326, and may be worn by the user on the exterior (i.e. outside the user's clothing) or on the inside of the user's clothing. The belt 1324 with the straps 1326 may be designed such that the belt 1324 may be tightened or loosened to cater for the different sizes of users. The belt 1324 further includes a first wing 1327a and a second wing 1327b. The first wing 1327a includes a Velcro fastener and the second wing 1327b includes a Velcro fastener. When the belt 1324 is worn by the user, the belt is wrapped around the body of the user and the first wing 1327a and the second wing 1327b may be adjustably fastened together to adapt the belt 1324 to the size of the user.

The first sensor 1322a, the second sensor 1322b, the third sensor 1322c and the fourth sensor 1322d, are movably arranged in the belt and therefore the positions of these sensors in the belt 1324 may be adjusted easily by the user. The first sensor 1322a, the second sensor 1322b, the third sensor 1322c and the fourth sensor 1322d may be covered by a soft layer of material 1328 for the comfort of the user. For aesthetic purposes and/or for use by children, the exterior side of the belt 1324 may be covered by an image, as shown in FIG. 13C.

In various embodiments, the first sensor 1322a, the second sensor 1322b, a third sensor 1322c and a fourth sensor 1322d, may be placed at positions corresponding to the neck (e.g. in proximity to the trachea or the upper airway), the right lung, the heart and the left lung, respectively, of a user's body, to receive sound signals originating from these internal organs. Therefore, sounds in the upper airway, the left and right lungs as well as the heart may be recorded and processed. The array of sensors may be placed at other positions, depending on the monitoring needs, at the back and in various positions around the chest area of the user. In various embodiments, by placing at least one sensor at a position corresponding to the heart of the user, the sensor may detect sounds originating from the heart and the left lung. Correspondingly, by placing at least, one sensor at a position corresponding to the left lung of the user, the sensor may detect sounds originating from the left lung and the heart.

For measurement operation, each of the first sensor 1322a, the second sensor 1322b, the third sensor 1322c and the fourth sensor 1322d, records and processes sounds received from the part of body respectively corresponding to each of the sensors, and the output results may be used together for monitoring purposes.

In various embodiments, the monitoring system 1320 may include circuitry, including a processing circuit, configured to perform monitoring of a health condition of the user. For example, the processing circuit may be configured to determine at least one entropy-based parameter value (e.g. an entropy difference between a maximum entropy value and a minimum entropy value and/or an entropy ratio of a maximum entropy value to a minimum entropy value). The processing circuit may include a memory for storage of results or data. The processing circuit may further include a wireless transmitter for communication with an external device (e.g. a database or a computer), where for example, a clinician may analyse the results or data. The processing circuit may further include at least one of a sound indicator and a light indicator configured to alert the user of the health condition.

In various embodiments, the processing circuit may be provided in a device in communication with the monitoring system 1320. The processing circuit may be configured to determine at least one entropy-based parameter value (e.g. an entropy difference between a maximum entropy value and a minimum entropy value and/or an entropy ratio of a maximum entropy value to a minimum entropy value). For communication between the monitoring system 1320 and the device, the monitoring system 1320 may include a wireless transmitter while the device may include a wireless receiver. The device may further include a wireless transmitter for communication with an external device (e.g. a database or a computer), where for example, a clinician may analyse the results or data. Each of the monitoring system 1320 and the device may also include a memory for storage of results or data. The device may further include a display, and at least one of a sound indicator and a light indicator. The device may be a mobile device (e.g. a personal digital assistant (PDA), a mobile phone or a smart phone).

While FIG. 13C shows an array of sensors 1321 having 4 sensors, any number of sensors may be provided, depending on the size and shape of the system and wearable design and the application of the system, for example 1 sensor, 2 sensors, 3 sensors, 5 sensors, 6 sensors or any higher number of sensors.

In various embodiments, each sensor of the array of sensors 1321 may be a microphone, a stethoscope, a piezo-electric device, a pressure-sensor, or any device that may be used to record sound or sound-generated signals, such that the array of sensors 1321 may include the same type of sensors or a combination of different types of sensors.

Figure 14:
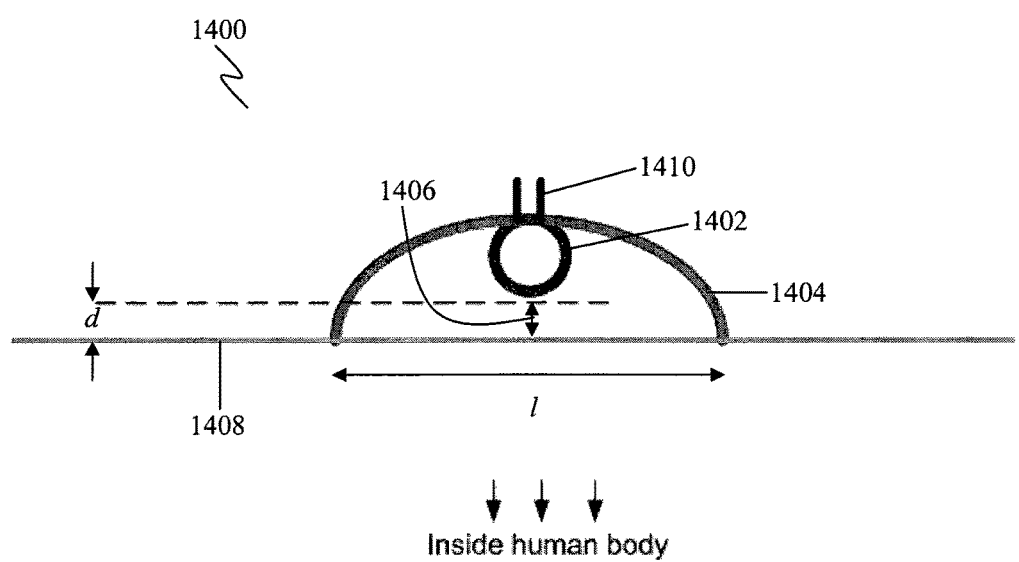
FIG. 14 shows a custom-designed microphone sensor, according to various embodiments.

FIG. 14 shows a custom-designed microphone sensor 1400, according to various embodiments. The custom-designed microphone sensor 1400 is a type of air conduction sensor. The custom-designed microphone sensor 1400 includes a microphone 1402 coupled to a housing 1404. The custom-designed microphone sensor 1400 is designed and configured such that an air gap 1406 is provided between the microphone 1402 and the skin or shirt 1408 worn by the user and that the area covered by the housing 1404 is larger than the area covered by the microphone 1402. In various embodiments, the housing 1404 may have a shape of a convex or a hemisphere or a square.

In various embodiments, the distance d of the air gap 1406 may be in a range of between about 0.1 cm to about 3 cm, for example a range of between about 0.1 cm to about 2 cm or a range of between about 1 cm to about 3 cm. In various embodiments, the diameter l of the housing 1404 may be in a range of between about 0.5 cm to about 6 cm, for example a range of between about 0.5 cm to about 3 cm, a range of between about 1.5 cm to about 6 cm or a range of between about 3 cm to about 6 cm. In various embodiments, the housing 1404 may cover an area in a range of between about 0.19 $cm^2$ to about 30 $cm^2$, for example a range of between about 0.19 $cm^2$ to about 20 $cm^2$, a range of between 0.19 $cm^2$ to about 10 $cm^2$ or a range of between 1 $cm^2$ to about 30 $cm^2$.

The microphone 1402 may be attached to a tube 1410 and connected to or in electrical communication with a filter and amplifier module (not shown).

In various embodiments, an e-stethoscope may be used to replace the microphone 1402 and the tube 1410.

A filter and amplifier module according to various embodiments will now be described below, by way of examples and not limitations.

Sounds or sound signals generated, for example, from the mouth, upper airway, chest, and/or back, are recorded by a respective sensor. Subsequently, the sounds received and recorded, for example, by each sensor of the array of external sensors 1302 (FIG. 13A), or the array of distributed external sensors 1316 (FIG. 13B) or the array of internal sensors 1321 (FIG. 13C) is respectively fed or transmitted to a filter and amplifier module (as illustrated in FIG. 11). Each of the filter and amplifier modules are designed and configured to suppress out-of-band noises and interferences, while amplifying the power of the target sound signals.

Table 1 shows the specifications of the filter and amplifier module of various embodiments.

TABLE 1

Specification of the filter and amplifier module

| Design Parameter | Specification |
| --- | --- |
| Filter bandwidth | 60 Hz to 4000 Hz |
| Amplifier Gain of Pass-Band | 0 dB to 30 dB |
| Attenuation of Stop-Band | 30 dB |

While the range for the filter bandwidth of the filter is between about 60 Hz to about 4000 Hz (4 kHz), it should be appreciated that the filter bandwidth may be in a range of 0 Hz to about 22.063 kHz (22063 Hz), for example a range of 0 Hz to about 16 kHz, a range of 0 Hz to about 10 kHz, a range of 0 Hz to about 4 kHz, a range of 4 kHz to about 22.063 kHz or a range of 4 kHz to about 16 kHz.

In addition, while the value for the attenuation of stop-band of the filter is about 30 dB, it should be appreciated that the attenuation of stop-band may be in a range of about 10 dB to about 80 dB, for example a range of about 10 dB to about 50 dB, a range of about 10 dB to about 30 dB, a range of about 30 dB to about 80 dB or a range of about 20 dB to about 60 dB.

In various embodiments, the amplifier may have a gain of pass-band in a range of between 0 dB to about 30 dB, for example a range of between 0 dB to about 20 dB, a range of between 0 dB to about 10 dB or a range of between about 10 dB to about 30 dB.

An analogue-to-digital Convertor (ADC) according to various embodiments will now be described below, by way of examples and not limitations.

In various embodiments, a multi-channel ADC may be provided for the monitoring system and portable system of various embodiments. In alternative embodiments, a single-channel ADC may be provided. The single-channel ADC may be a high speed single-channel ADC to sample the output signals of the sensors in turn, so long as the sampling rate is high enough.

Table 2 shows the specifications of the ADC of various embodiments.

TABLE 2

Specification of the analogue-to-dogotal converter

| Design Parameter | Specification |
| --- | --- |
| Sampling rate (Rs) | 8000 samples per second (sps) |
| Resolution | 16-bit |

While the value for the sampling rate of the ADC is about 8000 samples per second (sps), it should be appreciated that the sampling rate may be in a range of about 1000 sps to about 44.125 ksps (44125 sps), for example a range of 1000 sps to about 30000 sps, a range of 1000 sps to about 15000 sps, a range of 1000 sps to about 8000 sps, a range of 8000 sps to about 44125 sps or a range of 4000 sps to about 30000 sps.

In addition, while the value for the resolution of the ADC is 16-bit, it should be appreciated that the resolution may be in a range of 8-bit to 32-bit.

Theoretically, full signal recovery requires the signal to be sampled at above the Nyquist's rate and as such, practical systems are designed to sample signals at above the Nyquist' rate. Nyquist's rate refers to the lowest sampling rate that may permit accurate reconstruction of a sampled analogue signal and/or to avoid aliasing, equal to twice the highest frequency contained within the signal. Various embodiments of the system and method, for example for wheeze detection, may allow the signals to be sampled at below the Nyquist's rate. Various embodiments provide a method of sound signal detection even when the signals are sampled at below the Nyquist's rate. As the signals are sampled at below the Nyquist's rate, the system of various embodiments require a smaller amount of power, thereby reducing the power supply requirement and allowing the system to be wearable and portable.

A processor according to various embodiments will now be described below, by way of examples and not limitations.

Various embodiments may include a processor. The processor may include two modules, including a signal combining and noise reduction module and a wheeze signal detection module, for monitoring wheeze.

It should be appreciated that the processor may include any other module or modules as an alternative and/or in addition to the signal combining and noise reduction module and/or the wheeze signal detection module, depending on the applications of the system of various embodiments. For example, the wheeze signal detection module may be replaced by other module or modules configured to detect other respiratory sounds or signals or heart sounds.

A signal combining and noise reduction module according to various embodiments will now be described below, by way of examples and not limitations.

Figure 15A:
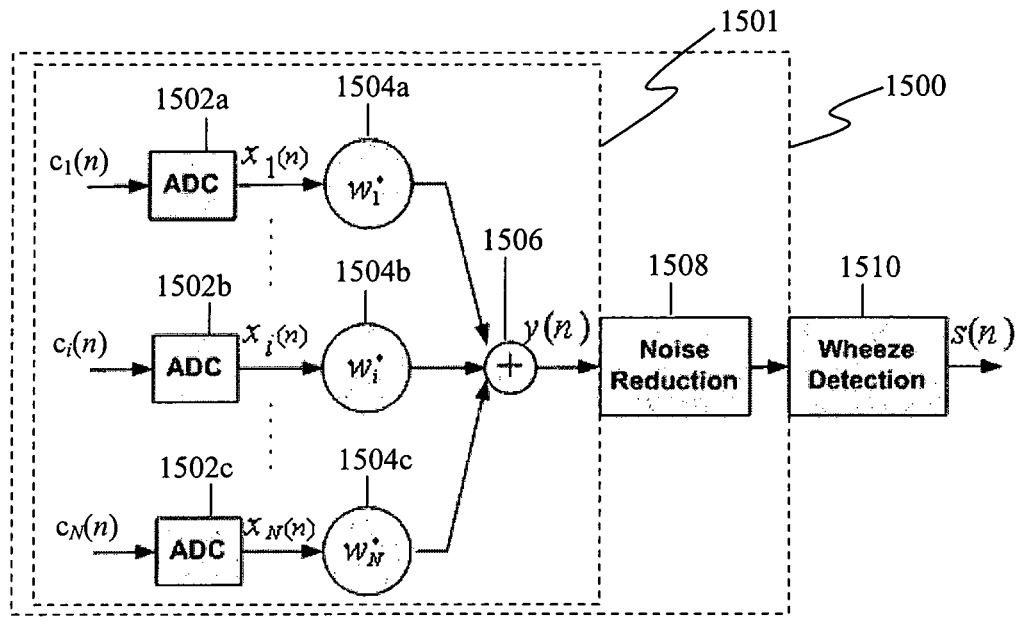
FIG. 15A shows a schematic block diagram of, a signal combining and noise reduction module, configured for use with a system with external sensors, according to various embodiments.

In embodiments of a portable system with external sensors, the signal combining operation is implemented through the use of a plurality of ADCs and a corresponding bank or plurality of filters. FIG. 15A shows a schematic block diagram of a, signal combining and noise reduction module 1500, configured for use with a system with external sensors, according to various embodiments. The schematic block diagram of the signal combining and noise reduction module 1500 includes a block diagram for a beamformer, as represented by the dotted box 1501, configured to perform the signal combining operation, and a noise reduction component 1508 (e.g. a temporal filter).

Beamforming is a signal processing technique used to mimimize the energy of all signals arriving from or transmitting to all directions except for the main beam direction where the signal of interest is arriving from or transmitting to. The technique may involve the use of a sensor array. Using beamforming, the majority of signal energy transmitted from an array of sensors may be directed in a particular angular direction. Conversely, the array of sensors may be configured to receive signals predominently from a particular angular direction. Therefore, a beamformer may receive sounds originating in one direction and suppress sounds in other directions.

As shown in FIG. 15A, an output signal, $c_1(n)$, from a first sensor (not shown) is sent to a first ADC 1502a. The first ADC 1502a then provides an output signal $x_1(n)$ to a first filter 1504a, which multiplies the output signal $x_1(n)$ with a complex value, $w_1$. Similarly, the output signals, $c_i(n)$ and $c_N(n)$, from an i-th sensor (not shown) and an N-th sensor (not shown) respectively, are sent respectively to an i-th ADC 1502b and an N-th ADC 1502c. The i-th ADC 1502b and the N-th ADC 1502c then respectively provide output signals $x_i(n)$ and $x_N(n)$ to an i-th filter 1504b and an N-th filter 1504c respectively. Subsequently, the i-th filter 1504b and the N-th filter 1504c, respectively multiply the output signals $x_i(n)$ and $x_N(n)$ with complex values, $w_i$ and $W_N$.

Subsequently, the resultant values from the first filter 1504a, the i-th filter 1504b and the N-th filter 1504c are summed together via a summing amplifier or a summer 1506 to produce a single output value y(n).

The signal y(n) (i.e. the output of the beamformer 1501) is then processed by the noise reduction component 1508 (e.g. a temporal filter) to further minimise the effect of noise and interferences. For example, one major type of interferences is speech, and hence a Blind Source Separation or a single-channel speech enhancement method may be implemented here with the noise reduction component 1508.

The output from the noise reduction component 1508 is then processed by a wheeze detection method, as represented by the block 1510, to produce a signal s(n) to indicate whether wheeze is present.

In various embodiments, the beamformer 1501 effectively functions as a spatial-domain filter where the desired or target signals, noise and interferences are separated based on their directions of arrivals.

It should be appreciated that there may be any number of ADCs and a corresponding number of filters, depending on the number of external sensors.

In various embodiments, the weights $w_1$, $w_i$ and $w_N$, respectively of the first filter 1504b, the i-th filter 1504b and the N-th filter 1504c, may be designed using a beamforming or beam pattern synthesis based method.

Figure 16:
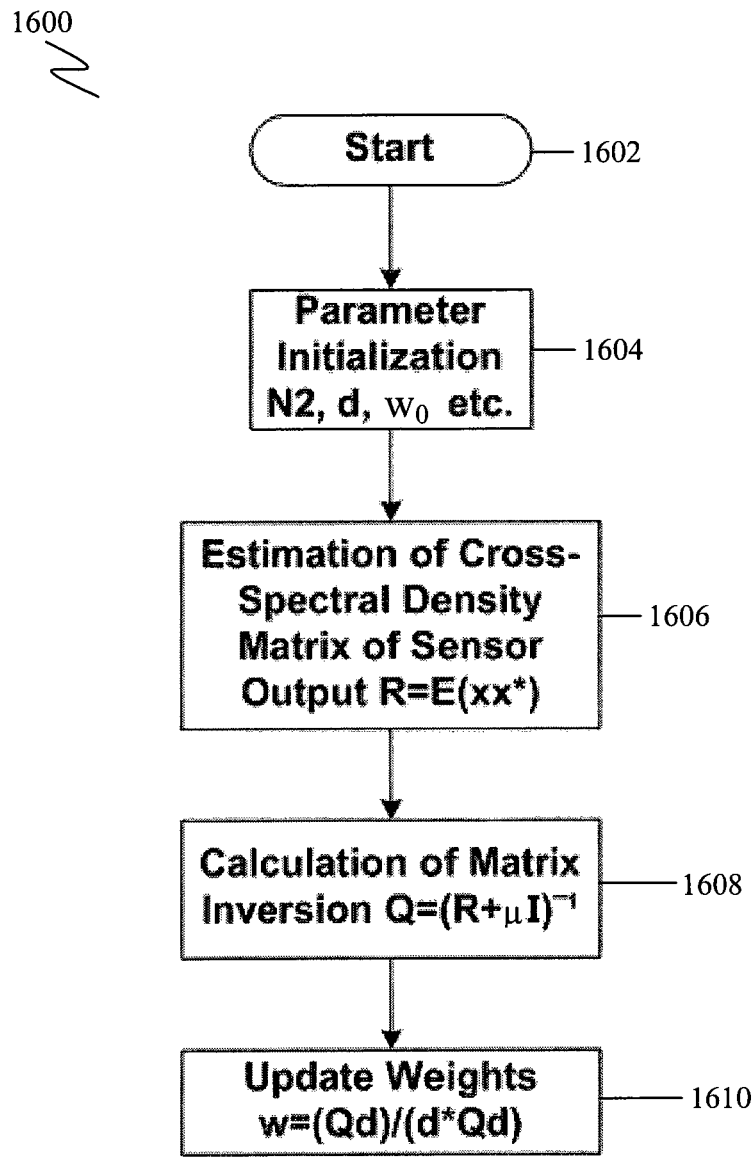
FIG. 16 shows a flow chart illustrating a beamforming-based calculation method, according to various embodiments.

FIG. 16 shows a flow chart 1600 illustrating a beamforming-based calculation method, according to various embodiments. After starting the method at 1602, the different parameters, e.g. N2, d, and $w_0$, are initialised at 1604. N2 represents a time duration (e.g. 3 seconds), d represents a vector where the elements of the vectors are the phase delays introduced by the various sensors, while $w_0$ represents the initial value of the weight, w, of the filter. For every time duration of N2, the co-variance matrix R of the sensor output x, is estimated at 1606 via the equation R=E[xx*], where x* is the complex conjugate of x, and E[xx*] is the Expected value of xx* as defined in Probability Theory. Subsequently, another matrix Q is calculated at 1608 via the equation $Q=(R+\mu I)^{-1}$, where $\mu$ is the Lagrange multiplier, I is the identity matrix and $(\ldots)^{-1}$ is the inverse of the matrix $(\ldots)$. The values of the weights $\{w_i\}$ of the filter is then determined at 1610 via the equation w=(Qd)/(d*Qd), where d* is the complex conjudate of d.

In various embodiments, the processes at 1606, 1608, and 1610 may be repeated periodically or continuously every N2 seconds to determine the values of $\{w_i\}$ so that the main beam direction is always pointing to the direction of the sound source.

In various embodiments, the value for the parameter is 0.0001. However, it should be appreciated that $\mu$ may be any value in a range of between 0 to about 1, for example a range of between 0 to about 0.8, a range of between 0 to about 0.5, a range of between 0 to about 0.3 or a range of between about 0.3 to about 1.

The respective weight of each filter is designed with the method of FIG. 16 so as to maintain the power of the target signals arriving from a particular direction (e.g. the main beam direction) and to suppress the unwanted noises and interferences arriving from other directions.

Figure 15B:
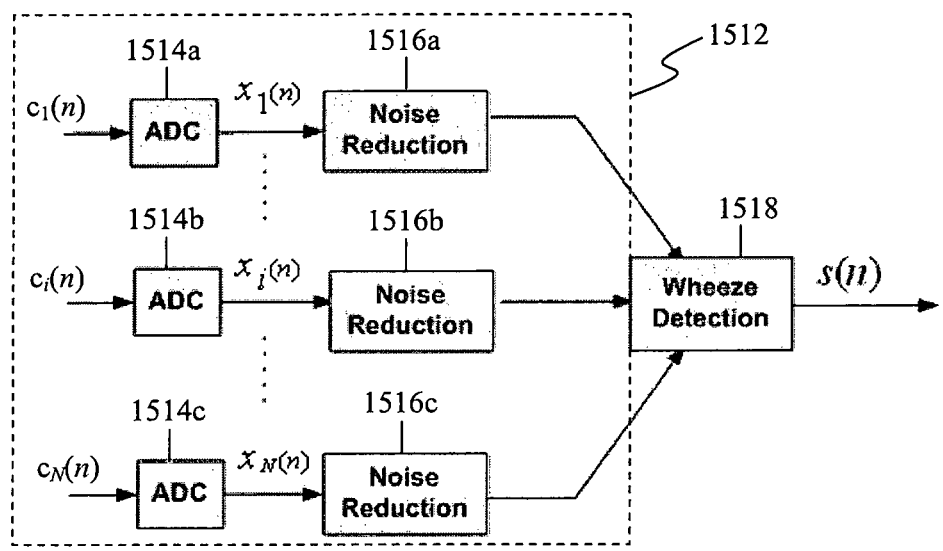
FIG. 15B shows a schematic block diagram of a signal combining and noise reduction module, configured for use with a system with internal sensors, according to various embodiments.

FIG. 15B shows a schematic block diagram of a signal combining and noise reduction module 1512, configured for use with a system with internal sensors, according to various embodiments. As shown in FIG. 15B, an output signal, $c_1(n)$, from a first sensor (not shown) is sent to a first ADC 1514a. Similarly, the output signals, $c_i(n)$ and $c_N(n)$, from an i-th sensor (not shown) and an N-th sensor (not shown) respectively, are sent respectively to an i-th ADC 1514b and an N-th ADC 1514c.

The output of each ADC is then fed to a noise reduction component (e.g. a temporal filter) to reduce the effect of noise and interferences before being combined. As shown in FIG. 15B, the first ADC 1514a provides an output signal $x_1(n)$ to a first noise reduction component 1516a, the i-th ADC 1514b provides an output signal $x_i(n)$ to an i-th noise reduction component 1516b while the N-th ADC 1514c provides an output signal $x_N(n)$ to an N-th noise reduction component 1516c.

Subsequently, the resultant values from the first noise reduction component 1516a, the i-th noise reduction component 1516b and the N-th noise reduction component 1516c are fed to a wheeze detection method, as represented by the block 1518, to produce a signal s(n) to indicate whether wheeze is present.

In the embodiments of FIGS. 15A and 15B, n represents the sample that is being processed, for example an n-th sample. For example, y(n) means the n-th sample of y.

In the embodiment of FIG. 15B, the output of each sensor is monitored and processed separately but the processed results from all the sensors are used together to indicate whether wheeze is present and provide a better understanding of the wheezing condition, for example whether the wheeze occurs in or relatively more in the upper airway, the left lung or the right lung and/or if poor heart rate occurs at the same time.

A wheeze signal detection method according to various embodiments will now be described below, by way of examples and not limitations.

An at least substantially similar wheeze signal detection method may be applied to the monitoring system and portable system with external sensors and the monitoring system and portable system with internal sensors. The wheeze signal detection method may be performed at a portable platform (e.g. a PDA or a mobile phone) as part of the portable system.

The wheeze signal detection method (e.g. the wheeze detection 1510 of the embodiment of FIG. 15A and the wheeze detection 1518 of the embodiment of FIG. 15B) is configured to process the output of the signal combining and noise reduction operation (e.g. performed by the signal combining and noise reduction module 1501 of the embodiment of FIG. 15A and the signal combining and noise reduction module 1512 of the embodiment of FIG. 15B).

In various embodiments, the wheeze detection scheme may be implemented via three stages. Stage 1 involves data segmentation, stage 2 involves entropy-based parameter value calculations and stage 3 involves comparison of the entropy-based parameter values with a threshold value. The implementation or operation of the wheeze detection scheme may be illustrated with reference to FIGS. 17, 18 and 19.

In various embodiments, prior to data segmentation, the signals captured or received by the external sensors or the internal sensors (e.g. microphones) may be sent to signal conditioning circuits for amplification, filtering and then conversion of the signals into digital signals.

Figure 17:
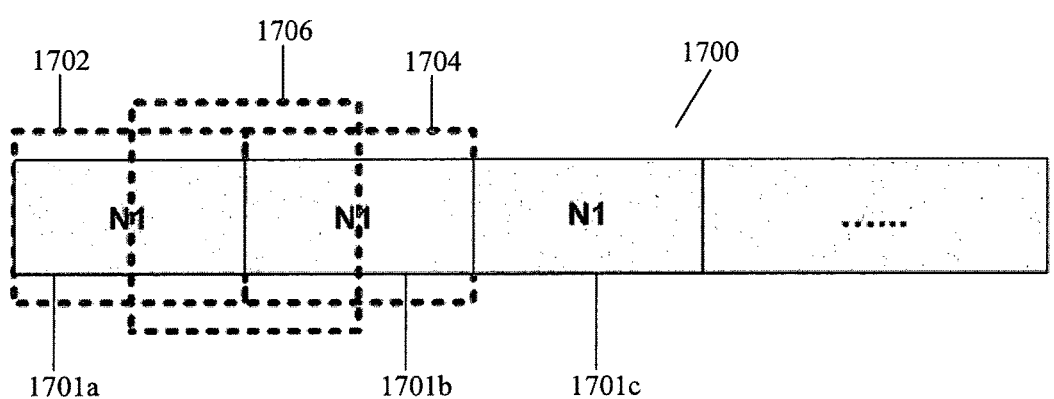
FIG. 17 illustrates data segmentation of a data stream, according to various embodiments.

FIG. 17 illustrates data segmentation of a data stream 1700, according to various embodiments. The process of data segmentation occurs before wheeze detection.

The data or data stream 1700 at the output of the signal combining and noise reduction module is stored in a buffer (e.g. memory) continuously. The data stream 1700 is then grouped into segments, each of which contains approximately N1 seconds of data. FIG. 17 illustrates as an example and not limitation, three segments of data, including a first data segment 1701a, a second data segment 1701 and a third data segment 1701c, where each segment contains N1 seconds of data. In various embodiments, the value for N1 is about 64 ms. However, it should be appreciated that N1 may be any value in a range of between about 10 ms to about 1 s (1000 ms), for example a range of between about 10 ms to about 500 ms, a range of between about 10 ms to about 200 ms, a range of between about 10 ms to about 64 ms, a range of between about 64 ms to about 1 s or a range of between about 200 ms to about 1 s.

A sliding window may then be used to select a portion of data stream 1700 (e.g. containing N samples) for wheeze detection. As shown in FIG. 17, a sliding window 1702 selects the first data segment 1701a for wheeze detection or a sliding window 1704 selects the second data segment 1701b for wheeze detection. In addition, a sliding window 1706 may instead select a data segment that overlaps the first data segment 1701a and the second data segment 1701b, for wheeze detection. In various embodiments with an overlap of data segments, the amount of overlap between two data segments is about 50%. However, it should be appreciated that the amount of overlap between two data segments may be in a range of between 0% to about 100%, for example a range of between 0% to about 80%, a range of between 0% to about 50%, a range of between 0% to about 20%, a range of between about 20% to 100% or a range of between about 50% to about 100%.

The use of a sliding window allows the same data or data segment 1700 to be used more than once for the wheeze detection scheme, which helps to improve the detection performance.

Figure 18:
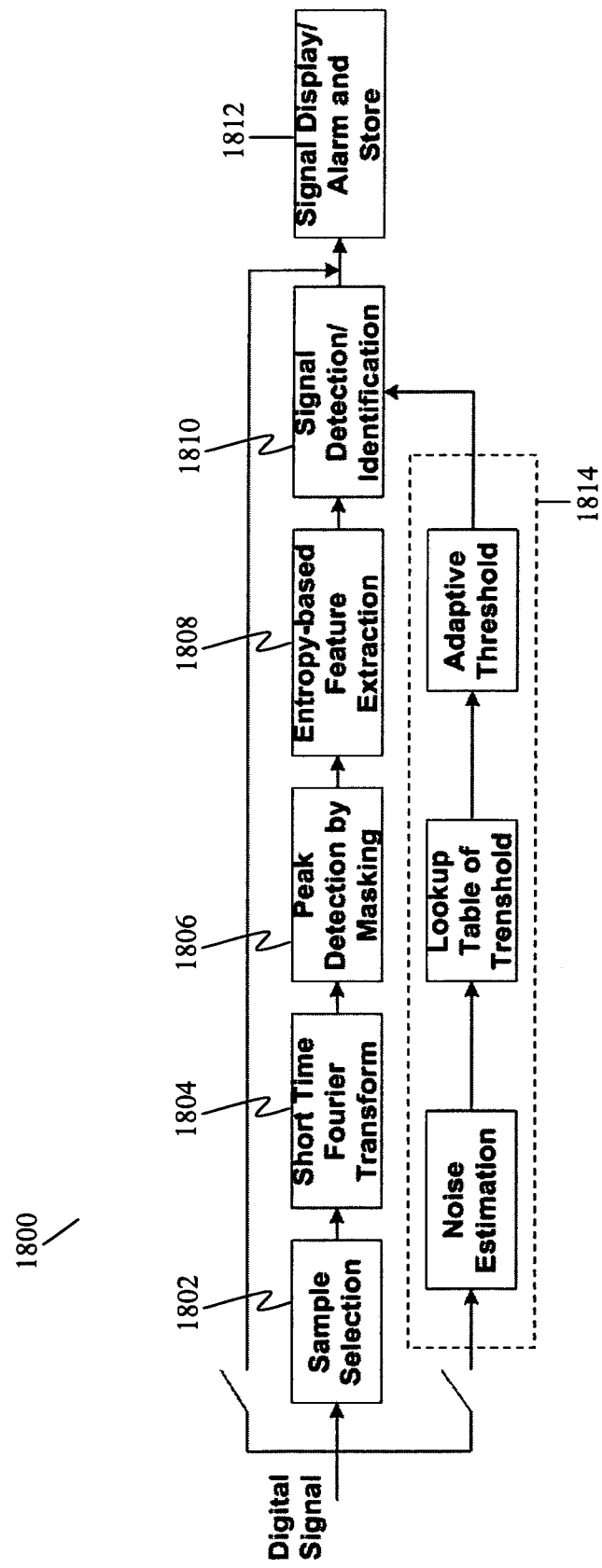
FIG. 18 shows a flow chart of a wheeze detection scheme, according to various embodiments.

FIG. 18 shows a flow chart 1800 of a wheeze detection scheme, according to various embodiments, following the selection of samples from the data segments, for example as illustrated in the embodiment of FIG. 17. The selected samples, for example the data selected by any of the sliding windows 1702, 1704, 1706, (FIG. 17) may optionally be subjected to a sample selection process 1802. The sample selection process 1802 reduces the number of samples for the purpose of either lowering the computational load or the removal of bad samples (e.g. errors). As an example and not limitation, the sample selection process 1802 may be implemented using a "Sub-Sampling" method. For example, the sub-sampling method may extract every K-th sample, where K is an integer, and uses the samples to form a final set of samples. As an example, the sub-sampling method with K=3 may be implemented such that, the $1^{st}$, $4^{th}$, $7^{th}$, $10^{th}$, . . . samples are extracted to form the final set of samples while the $2^{nd}$, $3^{rd}$, $5^{th}$, $6^{th}$, $8^{th}9^{th}$, . . . samples are discarded.

The selected data, for example of N samples, or the resultant data from the optional sample selection process 1802 is then transformed to the frequency domain by the use of a Short Time Fourier Transform (STFT) 1804 into a plurality of frequency components.

After transforming the selected samples into the frequency domain, a "Peak Detection" process 1806 is performed or implemented using a "Masking" or an "Averaging" filter. The use of an "Averaging" filter for peak detection reduces the number of components that need to be processed, and hence minimizes the processing and power requirements, e.g. reducing processing time and load and reducing power consumption.

The "Averaging" filter is used to select frequency components with dominant magnitudes (i.e. dominant frequency components) compared to those of adjacent frequency components, with non-dominant magnitudes (i.e. non-dominant frequency components).

This may be achieved by determining or computing the magnitudes of the components in a power spectrum corresponding to the STFT spectrum having the plurality of frequency components. The magnitude of each component of the power spectrum is first compared with a threshold point, $T_p$. When the magnitude of a component of the power spectrum is larger than $T_p$ (i.e. more than or above the value of $T_p$), the corresponding STFT component is identified as a peak (i.e. a dominant frequency component). The magnitude of the dominant frequency components may be denoted as $C_1, C_2, \ldots, C_D$, and may be used to calculate the entropy-based parameter values. If the magnitude of the component of the power spectrum is smaller than $T_p$ (i.e. less than or below the value of $T_p$), the corresponding STFT frequency component is considered a 'less significant frequency component' (i.e. a non-dominant frequency component). The non-dominant frequency components may be discarded and may not be used for further processing, thereby reducing the computational complexity.

In the context of various embodiments, the term "Entropy" of a parameter, p, is as defined in the Information Theory as Equation 2.

However, it should be noted that while the components of the power spectrum have been used as described above, the components of the STFT spectrum or other equivalents or variations may also be used for the same calculation. As an example, the magnitude of each STFT frequency component may be compared with the threshold point, $T_p$. In cases where the magnitude of the frequency component is larger than $T_p$, the frequency component is identified as a peak (i.e. a dominant frequency component). Otherwise, the frequency component is considered a 'less significant frequency component' (i.e. a non-dominant frequency component). The non-dominant frequency components may then be discarded.

The design of the "Masking" or "Averaging" filter is now described by way of example and not limitation. The threshold point $T_p$ may be determined by taking the average of the values of the M neighboring components of the power spectrum. Alternatively, the threshold point $T_p$ may be determined by taking the average of the values of the M neighboring frequency components. In various embodiments, the value of M is about a quarter of N (i.e. 0.25 of N or 0.25*N), with N being the number of samples selected from the data segments. However, it should be appreciated that M may be in a range of between 0 to N, for example a range of between 0 to 0.75*N, a range of between 0 to 0.5*N, a range of between 0 to 0.25*N, a range of between about 0.25*N to N or a range of between about 0.5*N to N.

In various embodiments, the magnitudes of the peaks of the selected STFT components (e.g. $C_1, C_2, \ldots, C_D$), being the dominant components, are used to determine or compute the entropy E of the dominant frequency components to provide a description of the balance of the power spectrum.

In various embodiments, the normalized power (or magnitude or equivalent), $p_n$, of the dominant frequency components may be determined from the equation:

$$p_n = \frac{C_n}{\sum_{n=1}^{D} C_n}, \quad \text{(Equation 1)}$$

where n is an element of $\{1, 2, \ldots, D\}$, D is the number of dominant frequency components and $C_n$ is a magnitude of each of the dominant frequency component.

As shown in equation 1, the normalized power, p, (or alternatively called the weight) for each dominant frequency component is determined by the proportion between the power of the specific dominant frequency component and the total power sum of all these dominant frequency components.

The entropy E of the dominant frequency components may then be determined from the normalized power, p, using the equation:

$$E = -\sum_{n=1}^{D} p_n \log(p_n), \quad \text{(Equation 2)}$$

In further embodiments, a modified entropy-based method may be implemented by replacing the magnitudes of the less significant frequency components (i.e. non-dominant frequency components) with suitable 'small values', instead of discarding them. These small values may be set to be equal to 0.01. These values may be assigned as the values for $C_{D+1}$, $C_{D+2}$, ..., and the value of the entropy E may be computed using equations 1 and 2, and by adding $C_{D+1}$+ $C_{D+2}$+ ... to the denominator of equation 1, where $C_{D+1}$, $C_{D+2}$, ... are the magnitudes of the non-dominant components. Correspondingly, n is an element of {1, 2, ..., D+1, D+2, ...} However, it should be noted that other values may be used, for example in a range between 0 to the smallest value or magnitude out of all the less significant frequency components. While this modified entropy-based method may increase complexity, it provides a better detection performance. The modified entropy-based method may allow to construct a time-feature improved entropy for periodic signals, which may be useful, for example in respiration monitoring.

Thereafter, an entropy-based feature extraction 1808 is performed after the peak detection process 1806.

In various embodiments, after smoothing the entropy for a sufficiently long duration N2, the maximum entropy value $E_{max}$ and the minimum entropy value $E_{min}$ are recorded or determined. The value for N2 is about 3 seconds. However, it should be appreciated that N2 may be of any value larger or longer than N1 (i.e. N2>N1), where N1 may be in a range of between about 10 ms to about 1 s (1000 ms). Therefore, N2 may be larger than about 10 ms (i.e. >10 ms), for example in a range of between about 10 ms to about 10 s, a range of between about 10 ms to about 5 s, a range of between about 10 ms to about 3 s, a range of between about 1 s to about 10 s, a range of between about 1 s to about 5 s, a range of between about 1 s to about 3 s or a range of between about 3 s to about 10 s.

The entropy-based feature extraction 1808 is then carried out to determine the entropy-based parameter value, $E_d$ (i.e. a difference between the maximum entropy value $E_{max}$ and the minimum entropy value $E_{min}$) and/or $E_r$ (i.e. a ratio of the maximum entropy value $E_{max}$ to the minimum entropy value $E_{min}$), from the following equations, respectively:

$$E_d = E_{max} - E_{min}, \quad \text{(Equation 3)}$$

$$E_r = \frac{E_{max}}{E_{min}}. \quad \text{(Equation 4)}$$

A signal detection or identification process 1810 is then performed to determine the presence of wheeze by identifying the signal of interest by observing whether the value of $E_d$ and/or $E_r$ has crossed a threshold value $T_E$. For example, the value of $E_d$ and/or $E_r$ is subtracted from the value of a threshold, $T_E$. In cases where the subtraction operation results in a positive value, the detection scheme determines that wheeze is present. Otherwise, wheeze is determined to be absent when the subtraction operation results in a negative value.

Subsequently, after the decision is made as to whether wheeze is present or absent, a signal display/alarm and store process 1812 may be performed to provide a signal indicator on a display and/or an alarm signal, and the results or data may be displayed, stored and/or transmitted to other devices for subsequent uses and/or processing.

Figure 19:
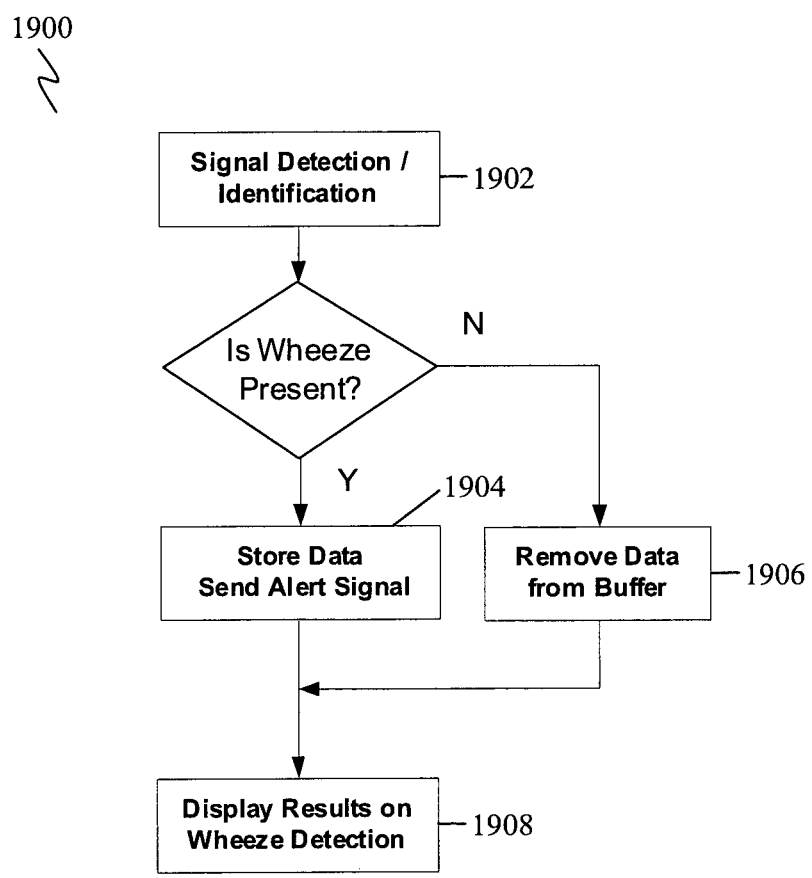
FIG. 19 shows a flow chart illustrating an operation of a wheeze recording scheme, according to various embodiments.

Referring to FIG. 18, the processes at 1810 and 1812 may be expanded in further details as shown in FIG. 19.

FIG. 19 shows a flow chart 1900 illustrating an operation of a wheeze recording scheme, according to various embodiments.

The signal detection or identification process at 1902 determines if wheeze is present or absent. If wheeze is detected to be present, the sample or data is stored and an alert signal (e.g. an alarm) may be sent, at 1904. If wheeze is detected to be absent, the sample or data is removed at 1906. After the processes of either 1904 or 1906, the detection/identification results are displayed, at 1908. The processes at 1904 and 1908 may be equivalent to 1812 (FIG. 18).

Figure 20:
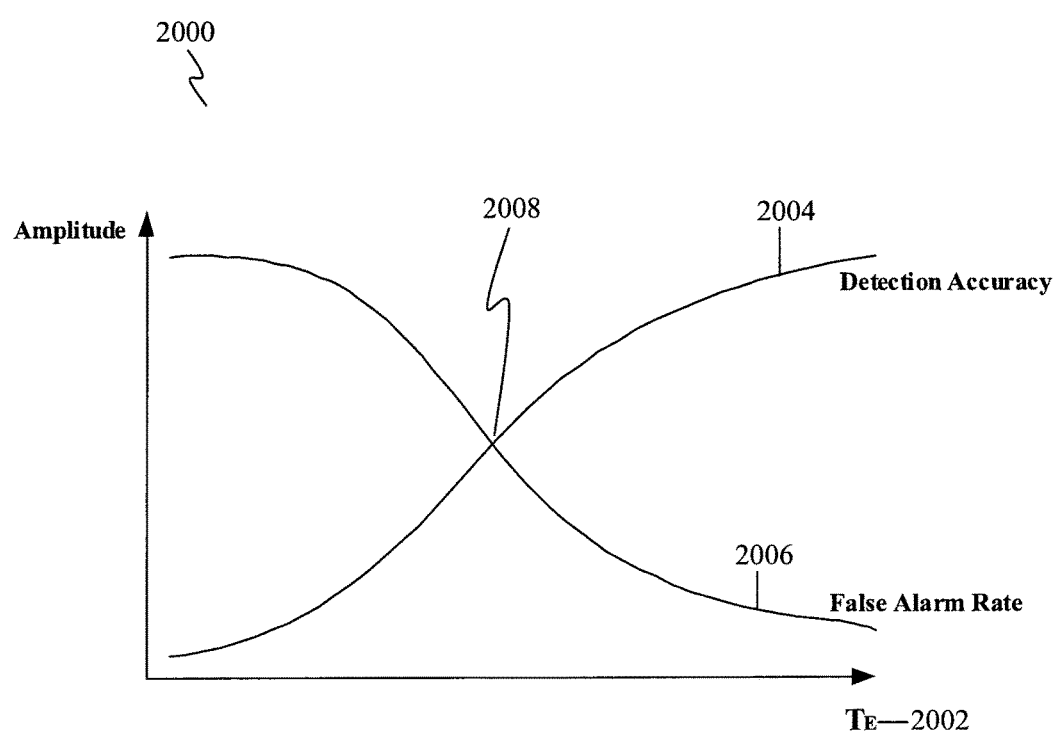
FIG. 20 shows a plot illustrating a relationship among $T_E$, detection accuracy and false alarm rate.

In various embodiments, the value of $T_E$ may either be fixed or adaptive (i.e. time-varying). For a fixed $T_E$, the value may be determined from the training samples as the value corresponding to the best detection accuracy and false alarm rate. In the context of various embodiments, training samples are samples collected under a controlled environment and they are used to determine the values of $T_E$. Detection accuracy refers to the percentage (%) of correct detection (e.g. the process detects that wheeze is present when the sound signals include wheezes) while false alarm rate refers to the percentage (%) of incorrect detection (e.g. the process detects that wheeze is present when the sound signals do not include wheezes). FIG. 20 shows, by way of example and not limitation, a plot 2000 illustrating a typical relationship among $T_E$ 2002, detection accuracy 2004 and false alarm rate 2006. The detection accuracy 2004 and the false alarm rate 2006 may be determined for each value of $T_E$ considered using the training samples in order to obtain the plot 2000 of FIG. 20. Subsequently, the value of $T_E$ at the intersection point 2008 may be used as the $T_E$ to test the real samples obtained from patients under tests.

Referring to FIG. 18, the flow chart 1800 of a wheeze detection scheme may include an adaptive threshold scheme 1814, which is described in further details below with reference to FIG. 21.

Figure 21:
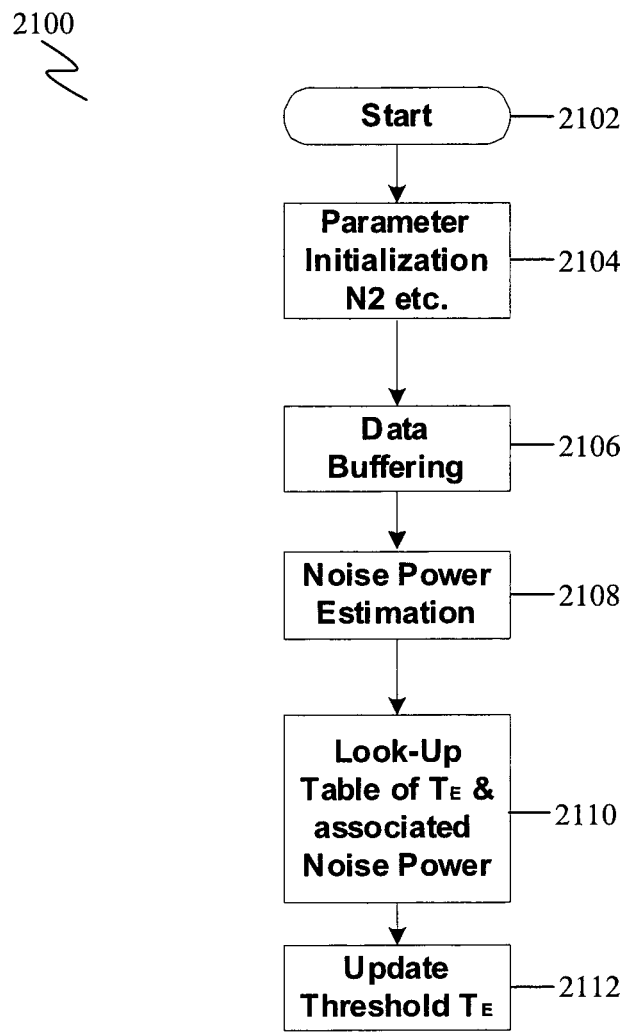
FIG. 21 shows a flow chart illustrating an adaptive threshold scheme, according to various embodiments.

FIG. 21 shows a flow chart 2100 illustrating an adaptive threshold scheme, according to various embodiments. In this scheme, the value of the threshold used changes according to the noise level experienced by the system of various embodiments.

After starting the scheme or method at 2102, the different parameters, e.g. N2, are initialised at 2104. Data buffering may then be carried out at 2106. At 2108, the components with very low magnitude (or power) (e.g. non-dominant frequency components) are assumed to contain no signal of interest but only noise. The power of these components are then taken as the estimated noise power. The value of the noise power obtained is then compared to those stored in a Look-Up Table (LUT) at 2110. The LUT stores both the values of $T_E$ obtained from FIG. 20 and the corresponding noise power considered when determining FIG. 20.

The value of $T_E$ corresponding to the estimated noise power is then used as the new value of $T_E$. When the estimated noise power varies, a new $T_E$ is used and the adaptive process continues as the sound signals are being processed. In this way, $T_E$ is updated, as shown by 2112. In various embodiments, the use of a Look-Up Table (LUT) for the selection of the adaptive threshold $T_E$ lowers the system complexity and hence the power requirement.

Various embodiments enable the use of a single parameter, e.g. the entropy-based parameter, to represent the energy distribution of the sound signals over the frequency spectrum. Various embodiments provide for the use of a single or two parameter values or features (e.g. $E_d$ and/or $E_r$) to determine the presence of wheeze or any other respiratory or cardiac conditions, instead of a larger number of parameters in conventional methods. This allows the detection process to be completed quickly and hence may be implemented using a much lower amount of power and hardware, thereby reducing the computational complexity and enabling the system of various embodiments to be wearable and portable, and with a much longer monitoring duration, compared to conventional methods.

A storage and a display according to various embodiments will now be described below, by way of examples and not limitations.

In various embodiments, the system or portable system for monitoring a health condition of a user of various embodiments may include a memory which is for example used in the processing carried out by the system or the portable system. In various embodiments, the memory may be provided and/or integrated with the Processing and Recording Sub-System (PRS) and/or with the monitoring system of various embodiments. The memory may be used for data storage, such as storing the parameter values extracted, as described in the above processes, for the indication of the presence of wheeze signals. In addition, in occasions where signals indicate wheeze is present, the raw data or sounds corresponding to the wheeze may be stored in the memory. Furthermore, various embodiments may provide that the presence of wheeze signals may be indicated by a light indicator, for example on a screen of the PRS or on an external display device.

In the context of various embodiments, a memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

The performance of the system and method of various embodiments is evaluated using sounds from the lungs of patients and normal subjects. The validity of the method of various embodiments was tested and the results are shown in FIG. 22A, evaluated using sounds from the lungs of ten patients and seven normal subjects and FIG. 22B, evaluated using sounds from the lungs of eleven patients and one normal subject.

Figure 22A:
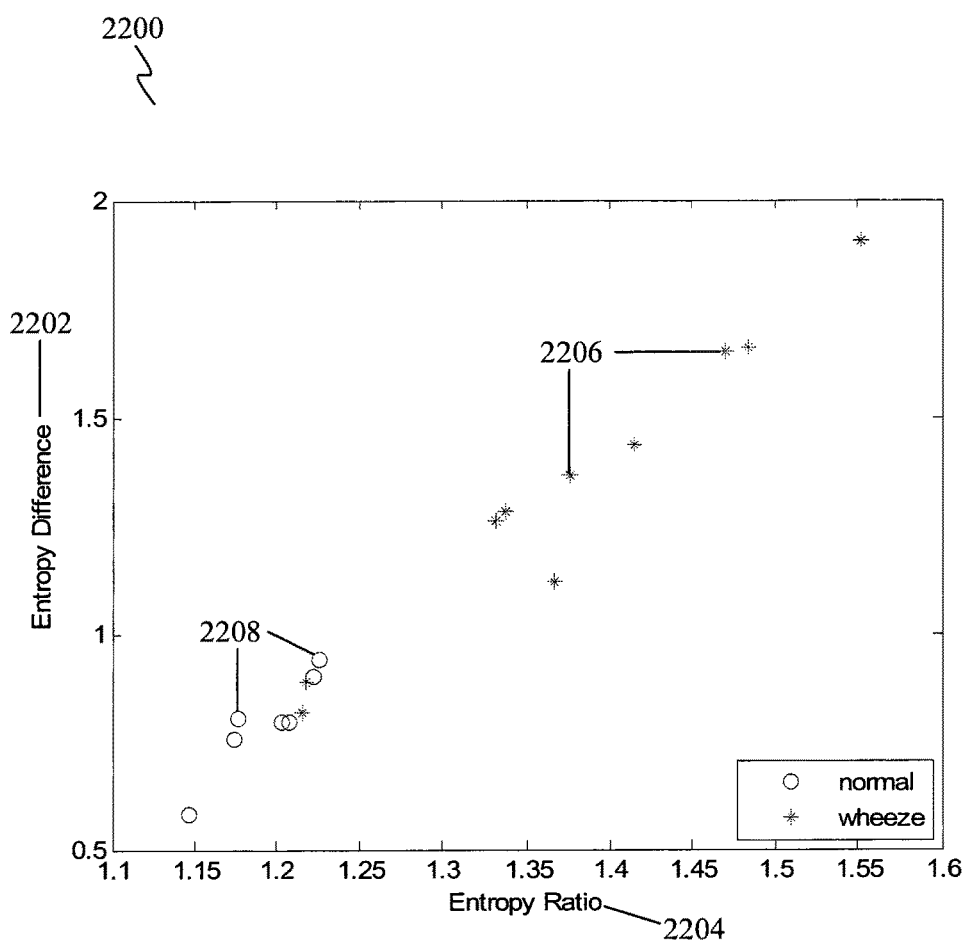
FIGS. 22A and 22B show plots of entropy difference and entropy ratio of human subjects, according to various embodiments.

FIG. 22A shows a plot 2200 of entropy difference 2202 and entropy ratio 2204 of human subjects, according to various embodiments. As shown in FIG. 22A, it may be observed that eight out of ten patients (star data points, as represented by 2206 for two such data points) may be distinguished from the normal subjects (circle data points, as represented by 2208 for two such data points), by either the entropy difference 2202 or the entropy ratio 2204 or both.

Figure 22B:
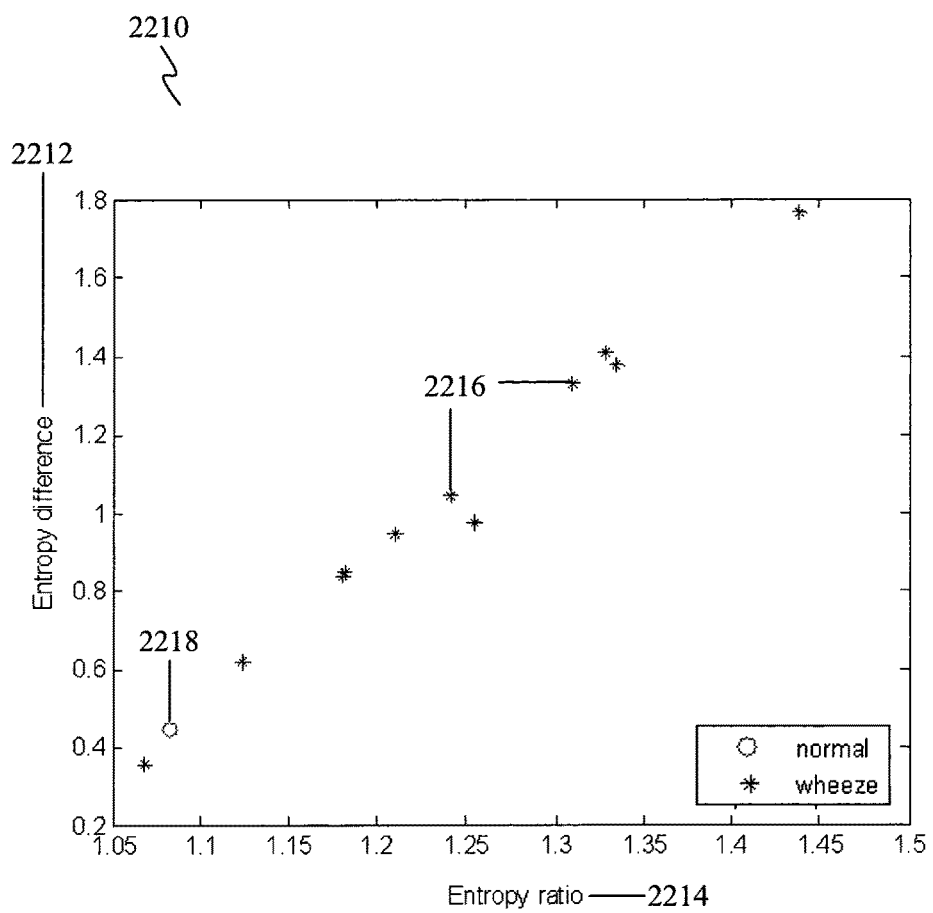

FIG. 22B shows a plot 2210 of entropy difference 2212 and entropy ratio 2214 of human subjects, according to various embodiments. As shown in FIG. 22B, it may be observed that ten out of eleven patients (star data points, as represented by 2216 for two such data points) may be distinguished from the normal subject (circle data points, as represented by 2218), by either the entropy difference 2212 or the entropy ratio 2214 or both.

In various embodiments, operation at below the Nyquist sampling rate may be implemented. The method of various embodiments were implemented with a wheezy breath in two operations, where the breath signals were sampled at approximately 2 kHz and approximately 1 kHz, respectively, to illustrate the principle that enables the method to work at down-sampling rates.

Figure 23:
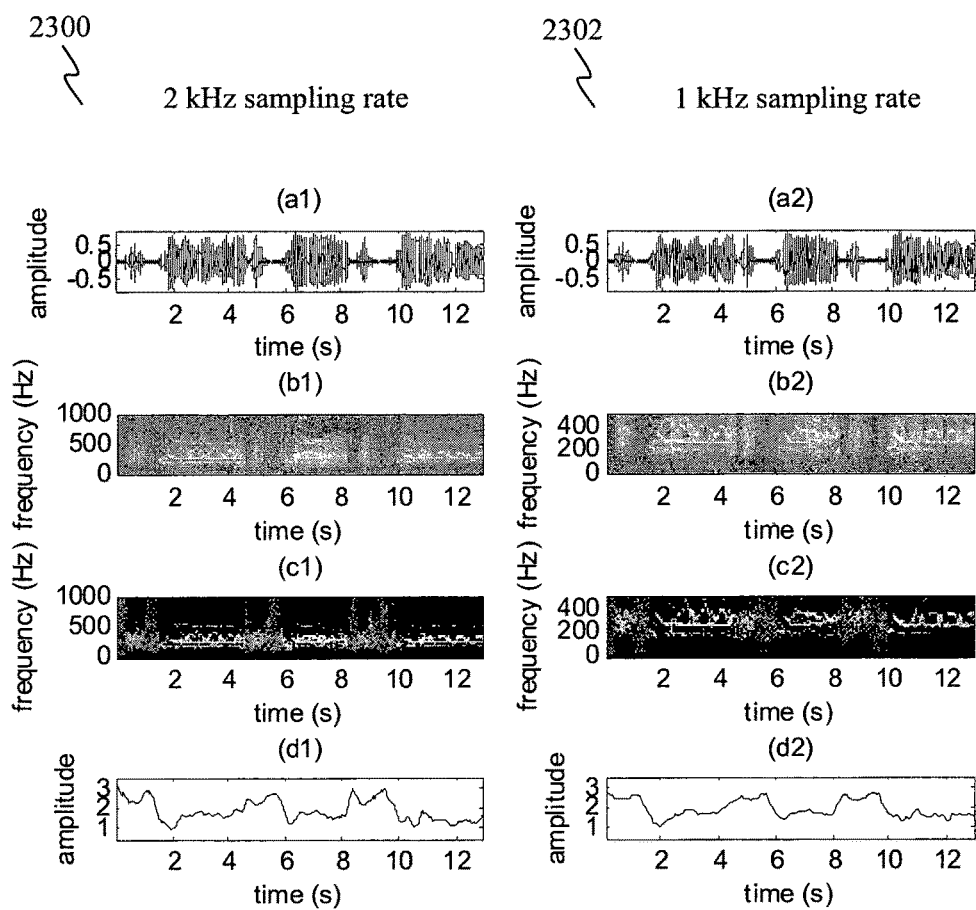
FIG. 23 shows results of entropy-based methods performed at below the Nyquist sampling rates, according to various embodiments.

The results from the main procedures of the operations of the entropy-based method at below the Nyquist sampling rates are shown in FIG. 23, where the left column 2300 of FIG. 23 (with images (a1), (b1), (c1) and (d1)) shows results for a wheezy breath sampled at approximately 2 kHz and the right column 2302 of FIG. 23 (with images (a2), (b2), (c2) and (d2)) shows results for the same wheezy breath but sampled at approximately 1 kHz.

Images (a1) and (a2) show the time-domain signals of the wheezy breath signals sampled at approximately 2 kHz and approximately 1 kHz, respectively. After STFT was performed on the time-domain signals of images (a1) and (a2), the respective frequency-domain signals (i.e. the frequency components) of the breath signals were obtained and are shown in images (b1) and (b2). It may be observed from the image (b1), corresponding to breath signals sampled at approximately 2 kHz, that there is a harmonic wheeze at about 520 Hz and a weaker harmonic wheeze at about 780 Hz. For the results shown in the image (b2), as the sampling rate of approximately 1 kHz is below twice of these harmonic frequencies (i.e. at about 520 Hz and about 780 Hz), a phenomenon known as frequency aliasing occurs, and as shown in the image (b2), these harmonic frequencies are translated to the spectrum in a range of 0 to about 500 Hz. Aliasing causes different signals to become indistinguishable and may present a serious problem to conventional signal detection methods or may even cause these conventional methods to fail. However, various embodiments provide a system and a method that allow the system and method to work even when the aliasing phenomenon occurs.

Images (c1) and (c2) show the results of peak detection. Frequency components below 70 Hz were removed in order to minimise interference from the power supply. As shown in the image (c2), even though frequency aliasing occurs, the peculiar energy distribution pattern of the wheezy signals are still maintained. As the method of various embodiments is based on the feature related to peculiar energy distribution pattern in terms of entropy, the frequency aliasing phenomenon does not substantially affect the fundamentals of the method.

Images (d1) and (d2) show the smoothened entropies for normal-sampled wheezy breath (i.e. sampled at about 2 kHz), and down-sampled wheezy breath (i.e. sampled at about 1 kHz), respectively. It may be observed that the method with down-sampling rate (i.e. image (d2)) show comparable performance to the method with normal sampling rate (i.e. image (d1)), at or above the Nyquist sampling rate.

Figure 24:
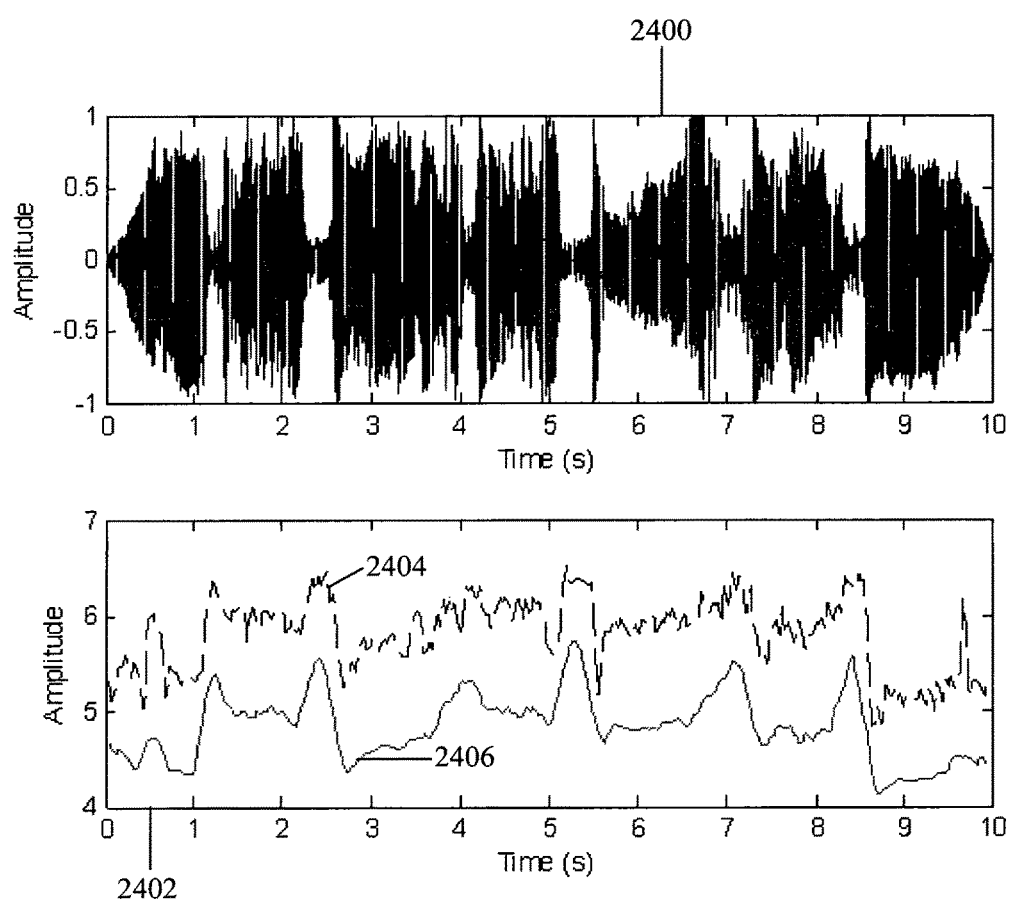
FIG. 24 shows results of a modified entropy-based method, according to various embodiments.

In addition, a modified entropy-based method was implemented by replacing the magnitudes of the less significant frequency components with a value of 0.01 and the results are shown in FIG. 24 for several breath signals sampled at approximately 8 kHz. FIG. 24 shows the time-domain signals 2400 and the smoothened entropy result 2402. The smoothened entropy result 2402 shows a comparison of results based on the entropy-based method 2404 and the modified entropy-based method 2406, illustrating a better performance (e.g. in terms of having sharper peaks in the time-domain plot) for the modified entropy-based method.

In order to evaluate the robustness of the system and the method of various embodiments against noise, the performances of the system and the method were evaluated at different levels of signal-to-noise ratios (SNRs) via computer simulations using real data and simulated noise. The SNR is defined as the ratio of the signal power to the noise power. In embodiments using a computer simulation test, the amount of noise added may be pre-determined and the corresponding SNR may be determined correspondingly.

Figure 25:
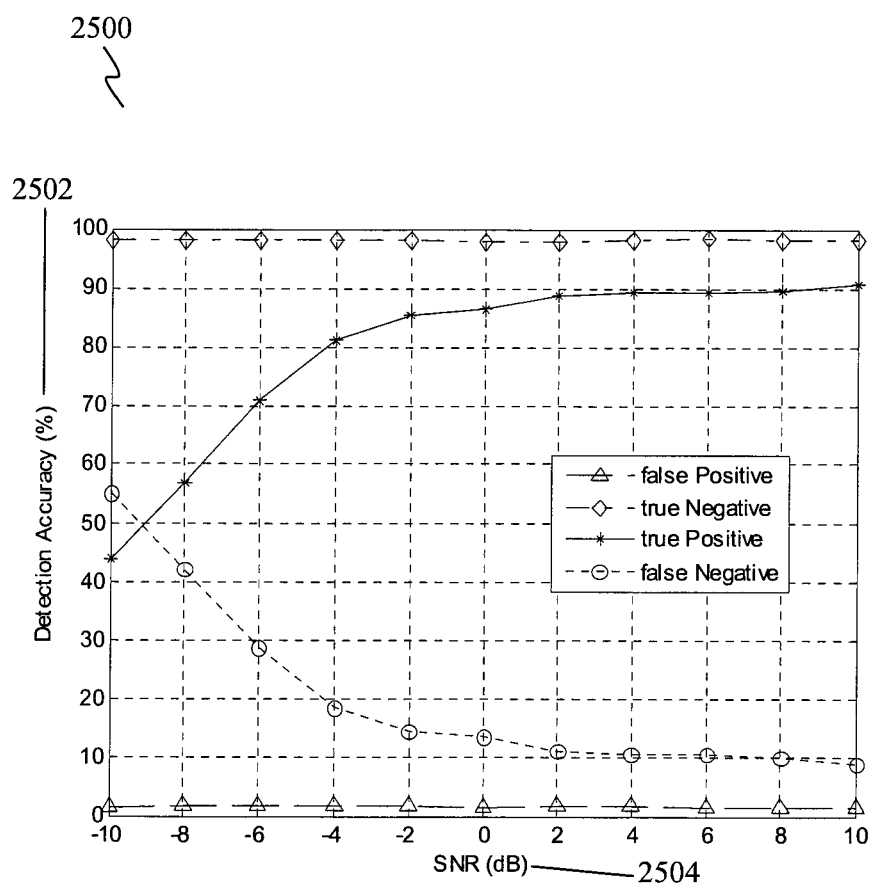
FIG. 25 shows performance results of the portable system with external sensors, according to various embodiments.

FIG. 25 shows performance results 2500 of the wearable portable system with external sensors, according to various embodiments. The detection accuracy of the system was evaluated at different levels of signal-to-noise ratios (SNRs) by computer simulations using real data and simulated noise. The performance results 2500 are shown in terms of detection accuracy (%) 2502 against SNR (expressed in dB) 2504. In the simulation, 63 breath samples including four normal breaths and 59 wheezy breaths were used. The levels of SNR is known during the simulation as the amount of noise added may be pre-determined for the computer simulation. The performance results 2500 show that the method of various embodiments may be able to produce good results for true positive, false positive, true negative, and false negative, which are important in the medical field.

In the context of various embodiments, the term "true positive" may mean that a sick person is correctly identified as sick, the term "false positive" may mean that a healthy person is incorrectly identified as sick, the term "true negative" may mean that a healthy person is correctly identified as healthy, and the term "false negative" may mean that a sick person is incorrectly identified as healthy.

Referring to FIG. 25, the performance results 2500 show that in terms of false positive, there is almost substantially zero probability of wrongly detecting healthy people as being sick; in terms of true negative, there is almost substantially 100% of correctly detecting healthy people as being healthy, in terms of true positive, there is substantially a 90% accuracy of detecting sick people as sick, and in terms of false negative, there is a 10% error of detecting sick people as being healthy, even when additional noise is added to the real samples collected.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A system for monitoring a health condition of a user, comprising:
an air conduction sensor for detecting a sound from the user, comprising:
a housing comprising an opening, wherein a rim of the opening is configured to be disposed on a skin or a clothing of the user; and
a microphone coupled to the housing such that there is an air gap between the microphone and the skin or the clothing, wherein the microphone is configured to detect the sound,
a filter and an amplifier in electrical communication with the microphone, the filter and the amplifier configured to process the sound;
an analogue-to-digital converter configured to convert the sound detected into a digital signal;
a selection circuit configured to select a predetermined number of samples from the digital signal;
a transformation circuit configured to transform the selected predetermined number of samples into a plurality of frequency components;
an entropy determination circuit configured to determine at least one entropy-based parameter value based on the plurality of frequency components; and
an entropy comparator circuit configured to compare the at least one entropy-based parameter value determined with a predetermined threshold value to detect a health signal for monitoring the health condition.

2. The system as claimed in claim 1, wherein the microphone is configured to detect the sound in a frequency ranging from 20 Hz to 20 kHz.

3. The system as claimed in claim 1, wherein the microphone is configured to convert the sound into an electrical signal.

4. The system as claimed in claim 1, wherein the air gap is in a range from 0.1 cm to 3 cm.

5. The system as claimed in claim 1, wherein the rim of the housing is configured to cover an area on the skin or the clothing in a range from 0.19 $cm^2$ to 30 $cm^2$.

6. The system as claimed in claim 1, wherein the housing has a shape of a hemisphere.

7. The system as claimed in claim 1, wherein the microphone is configured to detect the sound from at least one of a lung and a heart of the user.

8. A method for monitoring a health condition of a user, comprising:
detecting a sound from the user using an air conduction sensor the air conduction sensor comprising:
a housing comprising an opening, wherein a rim of the opening is configured to be disposed on a skin or a clothing of the user; and
a microphone coupled to the housing such that there is an air gap between the microphone and the skin or the clothing, wherein the microphone is configured to detect the sound;
processing the sound using a filter and an amplifier in electrical communication with the microphone;
converting the sound detected into a digital signal;
selecting a predetermined number of samples from the digital signal;
transforming the selected predetermined number of samples into a plurality of frequency components;
determining at least one entropy-based parameter value based on the plurality of frequency components; and
comparing the at least one entropy-based parameter value determined with a predetermined threshold value to detect a health signal for monitoring the health condition.

9. The method as claimed in claim 8, wherein the microphone is configured to detect the sound in a frequency ranging from 20 Hz to 20 kHz.

10. The method as claimed in claim 8, further comprising converting the sound into an electrical signal.

11. The method as claimed in claim 8, wherein the air gap is in a range from 0.1 cm to 3 cm.

12. The method as claimed in claim 8, wherein the rim of the housing is configured to cover an area on the skin or the clothing in a range from 0.19 $cm^2$ to 30 $cm^2$.

13. The method as claimed in claim 8, wherein the housing has a shape of a hemisphere.

14. The method as claimed in claim 8, detecting the sound comprises detecting the sound from at least one of a lung and a heart of the user.

15. The method according to claim 8,
wherein said determining at least one entropy-based parameter value comprises:

determining a plurality of entropy values based on the plurality of frequency components over a first time duration;

determining a maximum entropy value and a minimum entropy value from the plurality of entropy values over the first time duration, and determining the at least one entropy-based parameter value based on at least one of an entropy difference between the maximum entropy value and the minimum entropy value and an entropy ratio of the maximum entropy value to the minimum entropy value.

16. The method according to claim 15, further comprising:

segmenting the digital signal into a plurality of segments of a second time duration, wherein selecting the samples comprises selecting from the plurality of segments.

17. The system according to claim 1,
wherein the entropy determination circuit is configured to:

determine a plurality of entropy values based on the plurality of frequency components over a first time duration;

determine a maximum entropy value and a minimum entropy value from the plurality of entropy values over the first time duration, and determine the at least one entropy-based parameter value based on at least one of an entropy difference between the maximum entropy value and the minimum entropy value and an entropy ratio of the maximum entropy value to the minimum entropy value.

18. The system according to claim 17, further comprising a segmentation circuit configured to segment the digital signal into a plurality of segments of a second time duration, wherein the selection circuit is configured to select the samples from the plurality of segments.

* * * * *